(12) United States Patent
Weitz et al.

(10) Patent No.: US 10,316,873 B2
(45) Date of Patent: Jun. 11, 2019

(54) METHOD AND APPARATUS FOR FORMING MULTIPLE EMULSIONS

(71) Applicants: David A. Weitz, Bolton, MA (US); Darren Roy Link, Lexington, MA (US); Andrew S. Utada, Japan (JP)

(72) Inventors: David A. Weitz, Bolton, MA (US); Darren Roy Link, Lexington, MA (US); Andrew S. Utada, Japan (JP)

(73) Assignee: President and Fellows of Harvard College, Cambridge, MA (US)

( * ) Notice: Subject to any disclaimer, the term of this patent is extended or adjusted under 35 U.S.C. 154(b) by 701 days.

(21) Appl. No.: 14/681,560

(22) Filed: Apr. 8, 2015

(65) Prior Publication Data

US 2015/0285282 A1 Oct. 8, 2015

Related U.S. Application Data

(63) Continuation of application No. 11/885,306, filed as application No. PCT/US2006/007772 on Mar. 3, 2006, now Pat. No. 9,039,273.

(Continued)

(51) Int. Cl.
*A61K 9/127* (2006.01)
*A61K 9/113* (2006.01)
(Continued)

(52) U.S. Cl.
CPC .............. *F15D 1/008* (2013.01); *A61K 9/113* (2013.01); *A61K 9/1273* (2013.01);
(Continued)

(58) Field of Classification Search
CPC ....... F15D 1/008; A61K 9/113; A61K 9/1273; A61K 9/5089; B01F 13/0062;
(Continued)

(56) References Cited

U.S. PATENT DOCUMENTS 2,379,816 A 7/1945 Mabbs
2,918,263 A 12/1959 Eichhorn
(Continued)

FOREIGN PATENT DOCUMENTS

CH 563 807 A5 * 7/1975
CH 563807 A5 7/1975
(Continued)

OTHER PUBLICATIONS

Hawley's Condensed Chemical Dictionary, (2007), 499, John Wiley & Sons, Inc. Online @ http://onlinelibrary.wiley.com/book/10.1002/9780470114735/titles headwords = Emulsion, (downloaded Jan. 9, 2016), pp. 1.*

(Continued)

*Primary Examiner* — Stephen E Rieth
(74) *Attorney, Agent, or Firm* — Wolf, Greenfield & Sacks, P.C.

(57) ABSTRACT

The present invention generally relates to multiple emulsions, and to methods and apparatuses for making multiple emulsions. A multiple emulsion generally describes larger droplets that contain one or more smaller droplets therein. The larger droplets may be suspended in a third fluid in some cases. These can be useful for encapsulating species such as pharmaceutical agents, cells, chemicals, or the like. In some cases, one or more of the droplets can change form, for instance, to become solidified to form a microcapsule, a liposome, a polymerosome, or a colloidosome. Multiple emulsions can be formed in one step in certain embodiments, with generally precise repeatability, and can be tailored to include one, two, three, or more inner droplets within a single outer droplet (which droplets may all be nested in some cases).

16 Claims, 14 Drawing Sheets

Related U.S. Application Data

(60) Provisional application No. 60/659,045, filed on Mar. 4, 2005.

(51) Int. Cl.
*A61K 9/50* (2006.01)
*B01F 3/08* (2006.01)
*B01F 5/04* (2006.01)
*F15D 1/00* (2006.01)
*B01F 13/00* (2006.01)
*B82Y 30/00* (2011.01)
*B01F 5/00* (2006.01)
*B82Y 10/00* (2011.01)

(52) U.S. Cl.
CPC .......... *A61K 9/5089* (2013.01); *B01F 3/0807* (2013.01); *B01F 5/045* (2013.01); *B01F 5/046* (2013.01); *B01F 13/0059* (2013.01); *B01F 13/0062* (2013.01); *B82Y 30/00* (2013.01); *B01F 2005/0022* (2013.01); *B82Y 10/00* (2013.01); *Y10S 516/924* (2013.01); *Y10T 137/0391* (2015.04)

(58) Field of Classification Search
CPC .... B01F 13/0059; B01F 3/0807; B01F 5/045; B01F 5/046; B01F 2003/0823–2003/105; B01F 3/08–3/10; B01F 13/0071
See application file for complete search history.

(56) References Cited

U.S. PATENT DOCUMENTS

| | | |
|---|---|---|
| 3,505,244 A | 4/1970 | Cessna |
| 3,675,901 A | 7/1972 | Rion |
| 3,816,331 A | 6/1974 | Brown et al. |
| 3,980,541 A | 9/1976 | Aine |
| 4,251,195 A | 2/1981 | Suzuki et al. |
| 4,279,435 A | 7/1981 | Allred |
| 4,422,985 A | 12/1983 | Morishita et al. |
| 4,508,265 A | 4/1985 | Jido |
| 4,695,466 A | 9/1987 | Morishita et al. |
| 4,732,930 A | 3/1988 | Tanaka et al. |
| 4,743,507 A | 5/1988 | Franses et al. |
| 4,865,444 A | 9/1989 | Green et al. |
| 4,880,313 A | 11/1989 | Loquenz et al. |
| 4,888,140 A | 12/1989 | Schlameus et al. |
| 4,931,225 A | 6/1990 | Cheng |
| 4,978,483 A | 12/1990 | Redding, Jr. |
| 4,996,265 A | 2/1991 | Okubo et al. |
| 5,100,933 A | 3/1992 | Tanaka et al. |
| 5,149,625 A | 9/1992 | Church et al. |
| 5,204,112 A | 4/1993 | Hope et al. |
| 5,209,978 A | 5/1993 | Kosaka et al. |
| 5,216,096 A | 6/1993 | Hattori et al. |
| 5,232,712 A | 8/1993 | Mills et al. |
| 5,326,692 A | 7/1994 | Brinkley et al. |
| 5,378,957 A | 1/1995 | Kelly |
| 5,418,154 A | 5/1995 | Aebischer et al. |
| 5,452,955 A | 9/1995 | Lundstrom |
| 5,500,223 A | 3/1996 | Behan et al. |
| 5,512,131 A | 4/1996 | Kumar et al. |
| 5,617,997 A | 4/1997 | Kobayashi et al. |
| 5,681,600 A | 10/1997 | Antinone et al. |
| 5,762,775 A | 6/1998 | DePaoli et al. |
| 5,795,590 A | 8/1998 | Kiefer et al. |
| 5,849,055 A | 12/1998 | Arai et al. |
| 5,851,769 A | 12/1998 | Gray et al. |
| 5,882,680 A | 3/1999 | Suzuki et al. |
| 5,888,538 A | 3/1999 | Kiefer et al. |
| 5,935,331 A | 8/1999 | Naka et al. |
| 5,942,443 A | 8/1999 | Parce et al. |
| 5,980,936 A | 11/1999 | Krafft et al. |
| 6,046,056 A | 4/2000 | Parce et al. |
| 6,116,516 A | 9/2000 | Ganan-Calvo |
| 6,119,953 A | 9/2000 | Ganan-Calvo et al. |
| 6,120,666 A | 9/2000 | Jacobson et al. |
| 6,149,789 A | 11/2000 | Benecke et al. |
| 6,150,180 A | 11/2000 | Parce et al. |
| 6,174,469 B1 | 1/2001 | Ganan-Calvo |
| 6,187,214 B1 | 2/2001 | Ganan-Calvo |
| 6,189,803 B1 | 2/2001 | Ganan-Calvo |
| 6,193,951 B1 | 2/2001 | Ottoboni et al. |
| 6,196,525 B1 | 3/2001 | Ganan-Calvo |
| 6,197,835 B1 | 3/2001 | Ganan-Calvo |
| 6,221,654 B1 | 4/2001 | Quake et al. |
| 6,234,402 B1 | 5/2001 | Ganan-Calvo |
| 6,238,690 B1 | 5/2001 | Kiefer et al. |
| 6,241,159 B1 | 6/2001 | Ganan-Calvo et al. |
| 6,248,378 B1 | 6/2001 | Ganan-Calvo |
| 6,251,661 B1 | 6/2001 | Urabe et al. |
| 6,267,858 B1 | 7/2001 | Parce et al. |
| 6,274,337 B1 | 8/2001 | Parce et al. |
| 6,299,145 B1 | 10/2001 | Ganan-Calvo |
| 6,301,055 B1 | 10/2001 | Legrand et al. |
| 6,306,659 B1 | 10/2001 | Parce et al. |
| 6,355,198 B1 | 3/2002 | Kim et al. |
| 6,357,670 B2 | 3/2002 | Ganan-Calvo |
| 6,380,297 B1 | 4/2002 | Zion et al. |
| 6,386,463 B1 | 5/2002 | Ganan-Calvo |
| 6,394,429 B2 | 5/2002 | Ganan-Calvo |
| 6,399,389 B1 | 6/2002 | Parce et al. |
| 6,405,936 B1 | 6/2002 | Ganan-Calvo |
| 6,408,878 B2 | 6/2002 | Unger et al. |
| 6,429,025 B1 | 8/2002 | Parce et al. |
| 6,432,148 B1 | 8/2002 | Ganan-Calvo |
| 6,432,630 B1 | 8/2002 | Blankenstein |
| 6,450,189 B1 | 9/2002 | Ganan-Calvo |
| 6,464,886 B2 | 10/2002 | Ganan-Calvo |
| 6,489,103 B1 | 12/2002 | Griffiths et al. |
| 6,506,609 B1 | 1/2003 | Wada et al. |
| 6,508,988 B1 | 1/2003 | Van Dam et al. |
| 6,540,895 B1 | 4/2003 | Spence et al. |
| 6,554,202 B2 | 4/2003 | Ganan-Calvo |
| 6,557,834 B2 | 5/2003 | Ganan-Calvo |
| 6,558,944 B1 | 5/2003 | Parce et al. |
| 6,558,960 B1 | 5/2003 | Parce et al. |
| 6,560,030 B2 | 5/2003 | Legrand et al. |
| 6,592,821 B1 | 7/2003 | Wada et al. |
| 6,608,726 B2 | 8/2003 | Legrand et al. |
| 6,610,499 B1 | 8/2003 | Fulwyler et al. |
| 6,614,598 B1 | 9/2003 | Quake et al. |
| 6,630,353 B1 | 10/2003 | Parce et al. |
| 6,645,432 B1 | 11/2003 | Anderson et al. |
| 6,660,252 B2 | 12/2003 | Matathia et al. |
| 6,752,922 B2 | 7/2004 | Huang et al. |
| 6,790,328 B2 | 9/2004 | Jacobson et al. |
| 6,806,058 B2 | 10/2004 | Jesperson et al. |
| 6,890,487 B1 | 5/2005 | Sklar et al. |
| 6,935,768 B2 | 8/2005 | Lowe et al. |
| 7,041,481 B2 | 5/2006 | Anderson et al. |
| 7,068,874 B2 | 6/2006 | Wang et al. |
| 7,115,230 B2 | 10/2006 | Sundararajan et al. |
| 7,378,473 B2 * | 5/2008 | Torii ........................ C08F 2/44 137/3 |
| 7,651,770 B2 | 1/2010 | Berkland et al. |
| 7,708,949 B2 | 5/2010 | Stone et al. |
| 7,776,927 B2 * | 8/2010 | Chu ........................ A61K 9/113 347/55 |
| RE41,780 E | 9/2010 | Anderson et al. |
| 7,968,287 B2 | 6/2011 | Griffiths et al. |
| 8,302,880 B2 | 11/2012 | Clarke |
| 8,439,487 B2 | 5/2013 | Clarke et al. |
| 8,685,323 B2 | 4/2014 | Nam et al. |
| 8,696,952 B2 * | 4/2014 | Kumacheva .......... B01F 3/0807 264/4.1 |
| 8,697,008 B2 | 4/2014 | Clarke et al. |
| 8,741,192 B2 | 6/2014 | Torii et al. |
| 8,772,046 B2 | 7/2014 | Fraden et al. |
| 9,039,273 B2 | 5/2015 | Weitz et al. |
| 9,238,206 B2 * | 1/2016 | Rotem ................. B01F 3/0807 |
| 9,573,099 B2 | 2/2017 | Weitz et al. |
| 2002/0004532 A1 | 1/2002 | Matathia et al. |
| 2002/0008028 A1 | 1/2002 | Jacobson et al. |

(56) References Cited

U.S. PATENT DOCUMENTS

| | | |
|---|---|---|
| 2002/0119459 A1 | 8/2002 | Griffiths |
| 2003/0015425 A1 | 1/2003 | Bohm et al. |
| 2003/0039169 A1 | 2/2003 | Ehrfeld et al. |
| 2003/0077204 A1 | 4/2003 | Seki et al. |
| 2003/0124509 A1 | 7/2003 | Kenis et al. |
| 2003/0124586 A1 | 7/2003 | Griffiths et al. |
| 2003/0180485 A1 | 9/2003 | Nakajima et al. |
| 2003/0227820 A1 | 12/2003 | Parrent |
| 2004/0068019 A1* | 4/2004 | Higuchi ............ B01F 3/0807 516/9 |
| 2004/0096515 A1 | 5/2004 | Bausch et al. |
| 2004/0182712 A1 | 9/2004 | Basol |
| 2004/0266022 A1* | 12/2004 | Sundararajan ...... B01F 13/0062 436/180 |
| 2005/0032238 A1 | 2/2005 | Karp et al. |
| 2005/0032240 A1 | 2/2005 | Lee et al. |
| 2005/0172476 A1 | 8/2005 | Stone et al. |
| 2005/0183995 A1 | 8/2005 | Deshpande et al. |
| 2005/0207940 A1 | 9/2005 | Butler et al. |
| 2005/0221339 A1 | 10/2005 | Griffiths et al. |
| 2006/0014894 A1* | 1/2006 | Torii ............... C08F 2/44 524/801 |
| 2006/0051329 A1 | 3/2006 | Lee et al. |
| 2006/0078888 A1 | 4/2006 | Griffiths et al. |
| 2006/0078893 A1 | 4/2006 | Griffiths et al. |
| 2006/0108012 A1 | 5/2006 | Barrow et al. |
| 2006/0163385 A1 | 7/2006 | Link et al. |
| 2006/0263888 A1 | 11/2006 | Fritz et al. |
| 2007/0000342 A1 | 1/2007 | Kazuno |
| 2007/0003442 A1 | 1/2007 | Link et al. |
| 2007/0009668 A1 | 1/2007 | Wyman et al. |
| 2007/0054119 A1 | 3/2007 | Garstecki et al. |
| 2007/0056853 A1 | 3/2007 | Aizenberg et al. |
| 2007/0092914 A1 | 4/2007 | Griffiths et al. |
| 2007/0172873 A1 | 7/2007 | Brenner et al. |
| 2007/0195127 A1 | 8/2007 | Ahn et al. |
| 2007/0196397 A1 | 8/2007 | Torii et al. |
| 2008/0003142 A1 | 1/2008 | Link et al. |
| 2008/0004436 A1 | 1/2008 | Tawfik et al. |
| 2008/0014589 A1 | 1/2008 | Link et al. |
| 2009/0012187 A1 | 1/2009 | Chu et al. |
| 2009/0068170 A1 | 3/2009 | Weitz et al. |
| 2009/0131543 A1 | 5/2009 | Weitz et al. |
| 2009/0191276 A1 | 7/2009 | Kim et al. |
| 2010/0096088 A1 | 4/2010 | Okita et al. |
| 2010/0130369 A1 | 5/2010 | Shenderov et al. |
| 2010/0136544 A1 | 6/2010 | Agresti et al. |
| 2010/0137163 A1 | 6/2010 | Link et al. |
| 2010/0163109 A1 | 7/2010 | Fraden et al. |
| 2010/0170957 A1 | 7/2010 | Clarke |
| 2010/0173394 A1 | 7/2010 | Colston, Jr. et al. |
| 2010/0188466 A1 | 7/2010 | Clarke |
| 2010/0213628 A1 | 8/2010 | Bausch et al. |
| 2010/0238232 A1 | 9/2010 | Clarke et al. |
| 2011/0116993 A1 | 5/2011 | Nam et al. |
| 2011/0129941 A1* | 6/2011 | Kumacheva ......... A61K 9/1694 436/180 |
| 2011/0160078 A1 | 6/2011 | Fodor et al. |
| 2011/0229545 A1 | 9/2011 | Shum et al. |
| 2011/0305761 A1* | 12/2011 | Shum ............... A61K 9/1273 424/489 |
| 2012/0015382 A1 | 1/2012 | Weitz et al. |
| 2012/0048882 A1 | 3/2012 | Clarke et al. |
| 2012/0053250 A1 | 3/2012 | Carrick et al. |
| 2012/0199226 A1 | 8/2012 | Weitz et al. |
| 2012/0211084 A1* | 8/2012 | Weitz ............... B01F 3/0807 137/1 |
| 2012/0220494 A1 | 8/2012 | Samuels et al. |
| 2013/0046030 A1 | 2/2013 | Rotem et al. |
| 2013/0064862 A1 | 3/2013 | Weitz et al. |
| 2013/0274117 A1 | 10/2013 | Church et al. |
| 2013/0277461 A1 | 10/2013 | Ripoll et al. |
| 2013/0323764 A1 | 12/2013 | Nicholls et al. |
| 2014/0024023 A1 | 1/2014 | Cauley et al. |
| 2014/0065234 A1* | 3/2014 | Shum ............... A61K 9/1273 424/501 |
| 2014/0151912 A1 | 6/2014 | Nam et al. |
| 2014/0220350 A1 | 8/2014 | Kim et al. |
| 2014/0378349 A1 | 12/2014 | Hindson et al. |
| 2015/0005200 A1 | 1/2015 | Hindson et al. |
| 2016/0193574 A1 | 7/2016 | Weitz et al. |
| 2018/0071695 A1 | 3/2018 | Weitz et al. |

FOREIGN PATENT DOCUMENTS

| | | |
|---|---|---|
| CN | 1695809 A | 11/2005 |
| CN | 1933898 A | 3/2007 |
| CN | 102014871 A | 4/2011 |
| DE | 43 08 839 A1 | 9/1994 |
| DE | 199 61 257 A1 | 7/2001 |
| DE | 100 15 109 A1 | 10/2001 |
| DE | 100 41 823 A1 | 3/2002 |
| DE | 10200504825 A1 | 4/2007 |
| EP | 0 249 007 A2 | 12/1987 |
| EP | 0 272 659 A2 | 6/1988 |
| EP | 0 478 326 A1 | 4/1992 |
| EP | 0 718 038 B1 | 10/2002 |
| EP | 1 362 634 A1 | 11/2003 |
| EP | 1358931 A2 | 11/2003 |
| EP | 1362634 A1 | 11/2005 |
| EP | 1595597 A2 | 11/2005 |
| EP | 1 757 357 A1 | 2/2007 |
| EP | 1 741 482 A2 | 1/2008 |
| EP | 2 283 918 A2 | 2/2011 |
| EP | 2283918 A2 | 2/2011 |
| EP | 2 289 613 A2 | 3/2011 |
| FR | 2696658 A1 | 4/1994 |
| GB | 1 422 737 | 1/1976 |
| GB | 1 446 998 | 8/1976 |
| GB | 2 433 448 A | 6/2007 |
| JP | S54-107880 A | 8/1979 |
| JP | S56-130219 A | 10/1981 |
| JP | S60-040055 A | 3/1985 |
| JP | H10-219222 A | 8/1998 |
| JP | H11-509768 A | 8/1999 |
| JP | 2004-202476 A | 7/2004 |
| JP | 2004-351417 A | 12/2004 |
| JP | 2005-144356 A | 6/2005 |
| JP | 2005-152740 A | 6/2005 |
| JP | 2005-152773 A | 6/2005 |
| JP | 2005-288254 A | 10/2005 |
| JP | 2006-504512 A | 2/2006 |
| JP | 2006-507921 A | 3/2006 |
| JP | 2006-523142 A | 10/2006 |
| JP | 2008-073581 A | 4/2008 |
| JP | 2008-535644 A | 9/2008 |
| JP | 2008-238146 A | 10/2008 |
| JP | 2010-000428 A | 1/2010 |
| JP | 2011-041925 A | 3/2011 |
| JP | 5108875 B2 | 12/2012 |
| WO | WO 96/29629 A2 | 9/1996 |
| WO | WO 00/70080 A1 | 11/2000 |
| WO | WO 00/76673 A1 | 12/2000 |
| WO | WO 01/12327 A1 | 2/2001 |
| WO | WO 01/68257 A1 | 9/2001 |
| WO | WO 01/69289 A2 | 9/2001 |
| WO | WO 01/72431 A1 | 10/2001 |
| WO | WO 01/85138 A2 | 11/2001 |
| WO | WO 01/89787 A2 | 11/2001 |
| WO | WO 01/89788 A2 | 11/2001 |
| WO | WO 01/94635 A2 | 12/2001 |
| WO | WO 02/18949 A2 | 3/2002 |
| WO | WO 02/047665 A2 | 6/2002 |
| WO | WO 02/068104 A1 | 9/2002 |
| WO | WO 02/103011 A2 | 12/2002 |
| WO | WO 03/011443 A2 | 2/2003 |
| WO | WO 03/068381 A1 | 8/2003 |
| WO | WO 2004/002627 A2 | 1/2004 |
| WO | WO 2004/038363 A2 | 5/2004 |
| WO | WO 2004/052941 A1 * | 6/2004 |
| WO | WO 2004/071638 A2 | 8/2004 |
| WO | WO 2004/091763 A2 | 10/2004 |
| WO | WO 2005/002730 A1 | 1/2005 |

(56) References Cited

FOREIGN PATENT DOCUMENTS

| | | |
|---|---|---|
| WO | WO 2005/021151 A1 | 3/2005 |
| WO | WO 2005/049787 A2 | 6/2005 |
| WO | WO 2005/084210 A2 | 9/2005 |
| WO | WO 2005/089921 A1 | 9/2005 |
| WO | WO 2005/103106 A1 | 11/2005 |
| WO | WO 2006/002641 A1 | 1/2006 |
| WO | WO 2006/050638 A1 | 5/2006 |
| WO | WO 2006/078841 A1 | 7/2006 |
| WO | WO 2006/096571 A2 | 9/2006 |
| WO | WO 2006/101851 A2 | 9/2006 |
| WO | WO 2007/001448 A2 | 1/2007 |
| WO | WO 2007/081385 A2 | 7/2007 |
| WO | WO 2007/089541 A2 | 8/2007 |
| WO | WO 2008/058297 A2 | 5/2008 |
| WO | WO 2008/109176 A2 | 9/2008 |
| WO | WO 2008/121342 A2 | 10/2008 |
| WO | WO 2008/134153 A1 | 11/2008 |
| WO | WO 2009/000084 A1 | 12/2008 |
| WO | WO 2009/020633 A2 | 2/2009 |
| WO | WO 2009/048532 A2 | 4/2009 |
| WO | WO 2009/061372 A1 | 5/2009 |
| WO | WO 2009/120254 A1 | 10/2009 |
| WO | WO 2010/104597 A2 | 9/2010 |
| WO | WO 2010/104604 A1 | 9/2010 |
| WO | WO 2010/121307 A1 | 10/2010 |
| WO | WO 2011/028760 A2 | 3/2011 |
| WO | WO 2011/028764 A2 | 3/2011 |
| WO | WO 2012/048341 A1 | 4/2012 |

OTHER PUBLICATIONS

Nagai et al., "Solvent Removal During Curing Process of Highly Spheric and Monodispersed-Sized Polystyrene Capsules from Density-Matched Emulsions Composed of Water and Benzene/1,2-Dichloroethane," Journal of Polymer Science Part A: Polymer Chemistry, V. 38 Iss. 18 (Sep. 15, 2000): pp. 3412-3418.*
Okushima et al., "Controlled Production of Monodispersed Double Emulsions by Two-Step Droplet Breakup in Microfluidic Devices," Langmuir, (Nov. 9, 2004) 20, pp. 9905-9908 (Publication Date (Web): Oct. 8, 2004).*
Tan et al., Microfluidic Liposome Generation from Monodisperse Droplet Emulsion—Towards the Realization of Artificial Cells. Summer Bioengineering Conference Jun. 25-9, 2003. Key Biscayne, Florida. 2 pages.*
English language Translation on espacenet.com for CH 563 807 A5 (Jul. 15, 1975), (Battelle Memorial Institute), online @ https://worldwide.espacenet.com/ (Downloaded Dec. 16, 2016), pp. 1-10.*
Norimatsu et al., Recent research on target fabrication for upcoming projects, Fusion Engineering and Design 44 1999. 449-459.*
European Office Communication for EP 06737002.3 dated Apr. 3, 2008.
European Office Communication for EP 06737002.3 dated Mar. 11, 2009.
Examining Division Decision for EP 06737002.3 dated Sep. 2, 2010.
Extended European Search Report for EP 10165813.6 dated Oct. 7, 2010.
Invitation to Pay Additional Fees for PCT/US2006/007772 dated Jun. 28, 2006.
International Search Report and Written Opinion for PCT/US2006/007772 dated Sep. 1, 2006.
International Preliminary Report on Patentability for PCT/US2006/007772 dated Sep. 20, 2007.
Decision on Rejection for CN 200880017845.4 dated Sep. 24, 2012.
International Search Report and Written Opinion for PCT/US2008/004097 dated Aug. 10, 2009.
Korean Office Action for Application No. KR 10-2011-7000094 dated Feb. 27, 2013.
International Search Report and Written Opinion for International Application No. PCT/US09/003389 dated Oct. 21, 2009.
International Preliminary Report on Patentability for International Application No. PCT/US2009/003389 dated Dec. 16, 2010.
International Search Report and Written Opinion for International Application No. PCT/US2001/46181 dated Mar. 12, 2003.
International Preliminary Examination Report for International Application No. PCT/US2001/46181 dated Apr. 5, 2004.
International Search Report and Written Opinion for International Application No. PCT/US2007/084561 dated Apr. 29, 2008.
International Search Report and Written Opinion for PCT/US2010/000763 dated Jul. 20, 2010.
Chinese Office Action for Application No. CN 201080039018.2 dated Sep. 27, 2013.
Chinese Office Action dated May 13, 2014 for Application No. 201080039018.2.
Japanese Office Action dated Aug. 5, 2014 for Application No. JP 2012-527993.
International Search Report and Written Opinion for PCT/US2010/047458 dated May 24, 2011.
International Preliminary Report on Patentability for PCT/US2010/047458 dated Mar. 15, 2012.
Chinese Office Action for Application No. CN 201080039023.3 dated Dec. 23, 2013.
Chinese Office Action dated Oct. 24, 2014 for Application No. 201080039023.3.
Chinese Office Action dated Jul. 10, 2015 for Application No. 201080039023.3.
Extended European Search Report for Application No. EP 10814401.5 dated Nov. 3, 2015.
European Office Communication for EP 10814401.5 dated Nov. 10, 2016.
Japanese Office Action dated Jul. 22, 2014 for Application No. JP 2012-527995.
Japanese Office Action dated Jun. 11, 2015 for Application No. 2012-527995.
Korean Office Action dated Aug. 5, 2016 for Application No. KR 10-2012-7008201.
Office Action dated Feb. 16, 2017 for Application No. KR 10-2012-7008201.
Office Action dated Apr. 10, 2017 for Application No. KR 10-2012-7008201.
International Search Report and Written Opinion for PCT/US2010/047467 dated May 26, 2011.
International Preliminary Report on Patentability for PCT/US2010/047467 dated Mar. 15, 2012.
Chinese Office Action dated May 13, 2014 for Application No. CN 201180014139.6.
Invitation to Pay Additional Fees for PCT/US2011/028754 dated Nov. 30, 2011.
International Search Report and Written Opinion for PCT/US2011/028754 dated Apr. 3, 2012.
International Preliminary Report on Patentability for PCT/US2011/028754 dated Sep. 27, 2012.
Chinese Office Action dated Jan. 16, 2015 for Application No. CN 201280024857.6.
Chinese Office Action for Application No. CN 201280024857.6 dated Sep. 14, 2015.
European Office Action dated Mar. 24, 2015 for Application No. 12725967.9.
European Office Action for Application No. 12725967.9 dated Nov. 19, 2015.
Japanese Office Action for Application No. JP 2014-512944 dated Mar. 15, 2016.
Japanese Office Action dated Nov. 29, 2016 for Application No. JP 2014-512944.
Invitation to Pay Additional Fees for PCT/US2012/038957 dated Sep. 5, 2012.
International Search Report and Written Opinion for PCT/US2012/038957 dated Dec. 13, 2012.
International Preliminary Report on Patentability for PCT/US2012/038957 dated Dec. 5, 2013.

(56) References Cited

OTHER PUBLICATIONS

International Search Report and Written Opinion for PCT/US2012/045481 dated Feb. 6, 2013.
International Preliminary Report on Patentability for PCT/US2012/045481 dated Jan. 16, 2014.
Invitation to Pay Additional Fees dated May 31, 2013 for Application No. PCT/US2012/050916.
International Preliminary Report on Patentability dated Mar. 13, 2014 for Application No. PCT/US2012/050916.
Invitation to Pay Additional Fees dated Jul. 14, 2015 for Application No. PCT/US2015/025921.
International Search Report and Written Opinion dated Sep. 25, 2015 for Application No. PCT/US2015/025921.
International Preliminary Report on Patentability dated Oct. 27, 2016 for Application No. PCT/US2015/025921.
Office Communication for U.S. Appl. No. 11/885,306 dated May 31, 2011.
Office Communication for U.S. Appl. No. 11/885,306 dated Oct. 20, 2011.
Office Communication for U.S. Appl. No. 11/885,306 dated May 8, 2012.
Office Communication dated Oct. 9, 2014 for U.S. Appl. No. 11/885,306.
Office Communication for U.S. Appl. No. 12/058,628 dated Feb. 25, 2009.
Office Communication for U.S. Appl. No. 12/058,628 dated Sep. 1, 2009.
Office Communication for U.S. Appl. No. 12/993,205 dated Jul. 11, 2012.
Office Communication for U.S. Appl. No. 12/993,205 dated Feb. 14, 2013.
Office Communication for U.S. Appl. No. 10/433,753 dated Sep. 22, 2006.
Office Communication for U.S. Appl. No. 10/433,753 dated Oct. 3, 2008.
Office Communication for U.S. Appl. No. 10/433,753 dated May 28, 2009.
Office Communication for U.S. Appl. No. 12/019,454 dated Dec. 24, 2009.
Office Action for U.S. Appl. No. 13/388,596 dated Nov. 23, 2015.
Office Action dated Jun. 16, 2016 for U.S. Appl. No. 13/388,596.
Advisory Action dated Oct. 14, 2016 for U.S. Appl. No. 13/388,596.
Office Action for U.S. Appl. No. 13/388,596 dated Apr. 21, 2017.
Office Communication for U.S. Appl. No. 13/049,957 dated Feb. 1, 2013.
Office Communication for U.S. Appl. No. 13/049,957 dated Sep. 17, 2013.
Office Communication for U.S. Appl. No. 13/049,957 dated Feb. 21, 2014.
Ex Parte Quayle Action for U.S. Appl. No. 13/477,636 dated Aug. 3, 2015.
Office Communication for U.S. Appl. No. 13/586,628 dated Nov. 29, 2013.
Final Office Action dated Jun. 19, 2014 for U.S. Appl. No. 13/586,628.
[No Author Listed] ATP Determination Kit (A-22066). Molecular Probes. Product Information. 2003. 3 pages. Revised Apr. 23, 2003.
[No Author Listed] Experimental Soft Condensed Matter Group. Cool Picture of the Moment. Available at http://www.seas.harvard.edu/projects /weitzlab/coolpic16012007.html dated Jan. 16, 2007.
[No Author Listed], Toxnet, Toxicology Data Network. Vinyl Toluene. National Library of Medicine. 2015:1-38.
[No Author] "Paraffin Wax". http://www.wikipedia.com [last accessed Feb. 15, 2014].
[No Author] "Wax". http://www.wikipedia.com [last accessed Feb. 15, 2014].
[No Author] Microfluidic ChipShop. Microfluidic product catalogue. Mar. 2005.
[No Author] Microfluidic ChipShop. Microfluidic product catalogue. Oct. 2009.
Abate et al. One-step formation of multiple emulsions in microfluidics. Lab on a Chip. Lab Chip. Jan. 21, 2011;11(2):253-8. Epub Oct. 22, 2010. DOI:10.1039/C0LC00236D. 6 pages.
Abate et al., High-order multiple emulsions formed in poly(dimethylsiloxane) microfluidics. Small. Sep. 2009;5(18):2030-2.
Adams et al., Entropically driven microphase transitions in mixtures of colloidal rods and spheres. Nature. May 28, 1998:393:349-52.
Adams et al., Smart Capsules: Engineering new temperature and pressure sensitive materials with microfluidics. MAR10 Meeting of The American Physical Society. Mar. 15-19, 2010. Portland, Oregon. Submitted Nov. 20, 2009. Last accessed Jun. 14, 2012 at http://absimage.aps.org/image/MAR10/MWS_MAR10-2009-007422.pdf. Abstract only. 1 page.
Ahn et al., Dielectrophoretic manipulation of drops for high-speed microfluidic sorting devices. Applied Physics Letters. 2006;88:024104. 3 pages. Month not cited on publication.
Ando et al., PLGA microspheres containing plasmid DNA: preservation of supercoiled DNA via cryopreparation and carbohydrate stabilization. J Pharm Sci. Jan. 1999;88(1):126-30.
Anna et al., Formation of dispersions using "flow focusing" in microchannels. Applied Physics Letters. Jan. 20, 2003;82(3):364-6.
Benichou et al., Double Emulsions Stabilized by New Molecular Recognition Hybrids of Natural Polymers. Polym Adv Tehcnol. 2002;13:1019-31. Month not cited on publication.
Bibette et al., Emulsions: basic principles. Rep Prog Phys. 1999;62:969-1033. Month not cited on publication.
Boone, et al. Plastic advances microfluidic devices. The devices debuted in silicon and glass, but plastic fabrication may make them hugely successful in biotechnology application. Analytical Chemistry. Feb. 2002; 78A-86A.
Chang et al. Controlled double emulsification utilizing 3D PDMS microchannels. Journal of Micromechanics and Microengineering. May 9, 2008;18:1-8.
Chao et al., Control of Concentration and Volume Gradients in Microfluidic Droplet Arrays for Protein Crystallization Screening. 26th Annual International Conference of the IEEE Engineering in Medicine and Biology Society. Francisco, California. Sep. 1-5, 2004. 4 pages.
Chao et al., Droplet Arrays in Microfluidic Channels for Combinatorial Screening Assays. Hilton Head 2004: A Solid State Sensor, Actuator and Microsystems Workshop. Hilton Head Island, South Carolina. Jun. 6-10, 2004:382-3.
Chen et al., Capturing a photoexcited molecular structure through time-domain x-ray absorption fine structure. Science. Apr. 13, 2001;292(5515):262-4.
Chen et al., Microfluidic Switch for Embryo and Cell Sorting. The 12th International Conference on Solid State Sensors, Actuators, and Microsystems. Boston, MA. Jun. 8-12, 2003. Transducers. 2003:659-62.
Cheng et al., Electro flow focusing in microfluidic devices. Microfluidics Poster, presented at DEAS, "Frontiers in Nanoscience," presented Apr. 10, 2003. 1 page.
Chiba et al., Controlled protein delivery from biodegradable tyrosine-containing poly(anhydride-co-imide) microspheres. Biomaterials. Jul. 1997;18(13):893-901.
Chou, et al. Disposable Microdevices for DNA Analysis and Cell Sorting. Proc. Solid-State Sensor and Actuator Workshop, Hilton Head, SC. Jun. 8-11, 1998; 11-14.
Chu et al., Controllable monodisperse multiple emulsions. Ang Chem Int Ed. 2007:46:8970-4. Published online Sep. 11, 2007.
Cohen et al., Controlled delivery systems for proteins based on poly(lactic/glycolic acid) microspheres. Pharm Res. Jun. 1991;8(6):713-20.
Cole, Gelatin. Encyclopedia of Food Science and Technology. Second Ed. Francis, ed. 2000:1183-8. http://www.gelatin.co.za/gltn1.html [last accessed Feb. 15, 2014].
Collins et al., Microfluidic flow transducer based on the measurement of electrical admittance. Lab Chip. Feb. 2004;4(1):7-10. Epub Nov. 11, 2003. (E-pub version).

(56) References Cited

OTHER PUBLICATIONS

Collins et al., Optimization of Shear Driven Droplet Generation in a Microfluidic Device. ASME International Mechanical Engineering Congress and R&D Expo. Washington, D.C. Nov. 15-21, 2003. 4 pages.
Cortesi et al., Production of lipospheres as carriers for bioactive compounds. Biomaterials. Jun. 2002;23(11):2283-94.
Dendukuri et al. Continuous-flow lithography for high-throughput microparticle synthesis. Nature Mat. May 2006;5:365-69.
Diaz et al., One-month sustained release microspheres of $^{125}$I-bovine calcitonin In vitro-in vivo studies. Journal of Controlled Release. 1999;59:55-62. Month not cited on publication.
Dinsmore et al., Colloiclosomes: Selectively-Permeable Capsules Composed of Colloidal Particles. Supplementary Material (Nov. 2002). Available at http://people.umass.edu/dinsmore/pdf_files/colloidosome_supplementary.pdf . 6 pages.
Dinsmore et al., Colloidosomes: selectively permeable capsules composed of colloidal particles. Science. Nov. 1, 2002;298(5595):1006-9.
Discher et al., Polymersomes: tough vesicles made from diblock copolymers. Science. May 14, 1999;284(5417):1143-6.
Dove et al., Research News. Nature Biotechnology. Dec. 2002;20:1213.
Dowding et al., Oil core-polymer shell microcapsules prepared by internal phase separation from emulsion droplets. I. Characterization and release rates for microcapsules with polystyrene shells. Langmuir. Dec. 21, 2004;20(26):11374-9.
Durant et al., Effects of cross-linking on the morphology of structured latex particles 1. Theoretical considerations. Macromol. 1996;29:8466-72. Month not cited on publication.
Edris et al., Encapsulation of orange oil in a spray dried double emulsion. Nahrung/Food. Apr. 2001;45(2):133-7.
Eow et al., Electrocoalesce-separators for the separation of aqueous drops from a flowing dielectric viscous liquid. Separation and Purification Technology. 2002;29:63-77.
Eow et al., Electrostatic and hydrodynamic separation of aqueous drops in a flowing viscous oil. Chemical Engineering and Processing. 2002;41:649-57.
Eow et al., Electrostatic enhancement of coalescence of water droplets in oil: a review of the technology. Chemical Engineering Journal. 2002;85:357-68.
Eow et al., Motion, deformation and break-up of aqueous drops in oils under high electric field strengths. Chemical Engineering and Processing. 2003;42:259-72.
Eow et al., The behaviour of a liquid-liquid interface and drop-interface coalescence under the influence of an electric field. Colloids and Surfaces A: Physiochem Eng Aspects. 2003;215:101-23.
Estes et al., Electroformation of giant liposomes from spin-coated films of lipids. Colloids Surf B Biointerfaces. May 10, 2005;42(2):115-23.
Fisher et al., Cell Encapsulation on a Microfluidic Platform. The Eighth International Conference on Miniaturised Systems for Chemistry and Life Sciences. MicroTAS. Malmo, Sweden. Sep. 26-30, 2004. 3 pages.
Fu et al., A microfabricated fluorescence-activated cell sorter. Nat Biotechnol. Nov. 1999;17(11):1109-11.
Fujiwara et al., Calcium carbonate microcapsules encapsulating biomacromolecules. Chemical Engineering Journal. Feb. 13, 2008;137(1):14-22.
Fulwyler et al., Production of uniform microspheres. Rev Sci Instr. Feb. 1973;44(2):204-6.
Gallarate et al., On the stability of ascorbic acid in emulsified systems for topical and cosmetic use. Int J Pharm. Oct. 25, 1999;188(2):233-41.
Gañán-Calvo et al., Perfectly monodisperse microbubbling by capillary flow focusing. Phys Rev Lett. Dec. 31, 2001;87(27 Pt 1):274501. Epub Dec. 11, 2001. 4 pages.
Ganan-Calvo, Generation of Steady Liquid Microthreads and MicronSized Monodisperse Sprays in Gas Streams. Physical Review Letters. Jan. 12, 1998;80(2):285-8.

Ganan-Calvo, Perfectly monodisperse micro-bubble production by novel mechanical means. Scaling laws. American Physical Society 53$^{rd}$ Annual Meeting of the Division of Fluid Dynamics. Nov. 19-21, 2000. 1 page.
Gartner, et al. The Microfluidic Toolbox—examples for fluidic interfaces and standardization concepts. Proc. SPIE 4982, Microfluidics, BioMEMS, and Medical Microsystems, (Jan. 17, 2003); doi: 10.1117/12.479566.
Ghadessy et al. Directed evolution of polymerase function by compartmentalized self-replication. Proc Natl Acad Sci USA. Apr. 10, 2001; 98(8):4552-7. Epub Mar. 27, 2001.
Gordon et al., Self-assembled polymer membrane capsules inflated by osmotic pressure. JACS. 2004;126:14117-22. Published on web Oct. 12, 2004.
Graham et al., Nanogels and microgels: The new polymeric materials playground. Pure Appl Chem. 1998;70(6):1271-75. Month not cited on publication.
Grasland-Mongrain et al., Droplet coalescence in microfluidic devices. Jan.-Jul. 2003:1-30.
Griffiths et al., Man-made enzymes—from design to in vitro compartmentalisation. Curr Opin Biotechnol. Aug. 2000;11(4):338-53.
Griffiths et al., Miniaturising the Laboratory in Emulsion Droplets. Trends Biotechnol. Sep. 2006;24(9):395-402. Epub Jul. 14, 2006. (E-pub version).
Guery et al., Diffusion through colloidal shells under stress. Phys Rev E Stat Nonlin Soft Matter Phys. Jun. 2009;79(6 Pt 1):060402. Epub Jun. 29, 2009. 4 pages.
Gunther et al., Multiphase microfluidics: from flow characteristics to chemical and materials synthesis. Lab Chip. Sep. 27, 2006;6:1487-1503.
Hadd et al., Microchip device for performing enzyme assays. Anal Chem. Sep. 1, 1997;69(17):3407-12.
Hanes et al., Degradation of porous poly(anhydride-co-imide) microspheres and implications for controlled macromolecule delivery. Biomaterials. Jan.-Feb. 1998;19(1-3):163-72.
Hayward et al., Dewetting instability during the formation of polymersomes from block-copolymer-stabilized double emulsions. Langmuir. May 9, 2006;22(10):4457-61.
Hsu et al., Self-assembled shells composed of colloidal particles: fabrication and characterization. Langmuir. 2005;21:2963-70. Published on web Feb. 23, 2005.
Hug et al. Measurement of the number of molecules of a single mRNA species in a complex mRNA preparation. J Theor Biol. Apr. 21, 2003; 221(4):615-24.
Hung et al., Controlled Droplet Fusion in Microfluidic Devices. MicroTAS. Malmo, Sweden. Sep. 26-30, 2004. 3 pages.
Hung et al., Optimization of Droplet Generation by controlling PDMS Surface Hydrophobicity. 2004 ASME International Mechanical Engineering Congress and RD&D Expo. Anaheim, CA. Nov. 13-19, 2004. 2 pages.
Jang et al., Controllable delivery of non-viral DNA from porous scaffolds. J Control Release. Jan. 9, 2003;86(1):157-68.
Jo et al, Encapsulation of Bovine Serum Albumin in Temperature-Programmed "Shell-in-Shell" Structures. Macromol Rapid Commun. 2003;24:957-62. Month not cited on publication.
Jogun et al., Rheology and microstructure of dense suspensions of plate-shaped colloidal particles. J. Rheol. Jul./Aug. 1999;43:847-71.
Kanouni et al., Preparation of a stable double emulsion (W1/O/W2): role of the interfacial films on the stability of the system. Adv Colloid Interface Sci. Dec. 2, 2002;99(3):229-54.
Kawakatsu et al., Production of W/O/W emulsions and S/O/W pectin microcapsules by microchannel emulsification. Colloids and Surfaces. Jan. 2001;189:257-64.
Kim et al., Albumin loaded microsphere of amphiphilic poly(ethylene glycol)/poly($\alpha$-ester) multiblock copolymer. Eu. J. Pharm. Sci. 2004;23:245-51. Available online Sep. 27, 2004.
Kim et al., Colloidal assembly route for responsive colloidsomes with tunable permeability. Nano Lett. 2007;7:2876-80. Published on web Aug. 3, 2007.
Kim et al., Comparative study on sustained release of human growth hormone from semi-crystalline poly(L-lactic acid) and amorphous

(56) References Cited

OTHER PUBLICATIONS poly(D,L-lactic-co-glycolic acid) microspheres: morphological effect on protein release. J Control Release. Jul. 23, 2004;98(1):115-25.

Kim et al., Double-emulsion drops with ultra-thin shells for capsule templates. Lab Chip. Sep. 21, 2011;11(18):3162-6. Epub Aug. 2, 2011.

Kim et al., Fabrication of monodisperse gel shells and functional microgels in microfluidic devices. Angew Chem Int Ed. 2007;46:1819-22. Month not cited on publication.

Kim et al., Monodisperse nonspherical colloid materials with well-defined structures. Presentation. Sep. 16, 2005. 5 pages.

Kim et al., Synthesis of nonspherical colloidal particles with anisotropic properties. JACS. 2006;128:14374-77. Published on web Oct. 18, 2006.

Kim et al., Uniform nonspherical colloidal particles engineered by geometrically tunable gradient of crosslink density. $80^{th}$ ACS Colloid Surf. Sci. Symp. Jun. 20, 2006. 23 pages.

Kim et al., Uniform nonspherical colloidal particles with tunable shapes. Adv. Mater. 2007;19:2005-09. Month not cited on publication.

Koo et al., A snowman-like array of colloidal dimers for antireflecting surfaces. Adv Mater. Feb. 3, 2004;16(3):274-77.

Lamprecht et al., pH-sensitive microsphere delivery increases oral bioavailability of calcitonin. J Control Release. Jul. 23, 2004;98(1):1-9.

Landfester et al. Preparation of Polymer Particles in Nonaqueous Direct and Inverse Miniemulsions. Macromolecules. Mar. 11, 2000;33(7):2370-2376.

Landfester et al., Formulation and Stability Mechanisms of Polymerizable Miniemulsions. Macromolecules. 1999;32:5222-5228. Published on web Jul. 22, 1999.

Leary et al., Application of Advanced Cytometric and Molecular Technologies to Minimal Residual Disease Monitoring. In: In-Vitro Diagnostic Instrumentation. Gerald E. Cohn, Ed. Proceedings of SPIE. 2000;3913:36-44. Month not cited on publication.

Lee et al., Double emulsion-templated nanoparticle colloidosomes with selective permeability. Adv Mater. 2008;20:3498-503. Month not cited on publication.

Lee et al., Effective Formation of Silicone-in-Fluorocarbon-in-Water Double Emulsions: Studies on Droplet Morphology and Stability. Journal of Dispersion Science and Technology. 2002;23(4):491-7. Month not cited on publication.

Lee et al., Nonspherical colloidosomes with multiple compartments from double emulsions. Small. Sep. 2009;5(17):1932-5.

Lee et al., Preparation of Silica Particles Encapsulating Retinol Using O/W/O Multiple Emulsions. J Colloid Interface Sci. Aug. 1, 2001;240(1):83-89.

Lemoff et al., An AC Magnetohydrodynamic Microfluidic Switch for Micro Total Analysis Systems. Biomedical Microdevices. 2003;5(1):55-60. Month not cited on publication.

Li et al., PEGylated PLGA nanoparticles as protein carriers: synthesis, preparation and biodistribution in rats. Journal of Controlled Release. 2001;71:203-211. Month not cited on publication.

Lin et al., Ultrathin cross-linked nanoparticle membranes. JACS. 2003;125:12690-91. Published on web Sep. 27, 2003.

Link et al., Geometrically mediated breakup of drops in microfluidic devices. Phys Rev Lett. Feb. 6, 2004;92(5):054503. Epub Feb. 6, 2004. 4 pages.

Lopez-Herrera et al., Coaxial jets generated from electrified Taylor cones. Scaling laws. Aerosol Science. 2003:34:535-52. Month not cited on publication.

Lopez-Herrera et al., One-Dimensional Simulation of the Breakup of Capillary Jets of Conducting Liquids. Application to E.H.D. Spraying. J Aerosol Sci. 1999;30(7):895-912. Month not cited on publication.

Lopez-Herrera et al., The electrospraying of viscous and non-viscous semi-insulating liquids. Scalilng laws. Bulletin of the American Physical Society Nov. 1995;40:2041. Abstract JB 7.

Lorenceau et al., Generation of polymerosomes from double-emulsions. Langmuir. Sep. 27, 2005;21(20):9183-6.

Loscertales et al., Micro/nano encapsulation via electrified coaxial liquid jets. Science. Mar. 1, 2002;295(5560):1695-8.

Lundstrom et al., Breakthrough in cancer therapy: Encapsulation of drugs and viruses. www.currentdrugdiscovery.com. Nov. 2002:19-23.

Ly et al., Effect of Alcohols on Lipid Bilayer Rigidity, Stability, and Area/Molecule (in collaboration with David Block and Roland Faller). Available at http://www.chms.ucdavis.edu/research/web/longo/micromanipulation.html. Last accessed Oct. 10, 2012.

Magdassi et al., Formation of water/oil/water multiple emulsions with solid oil phase. J Coll Interface Sci. Dec. 1987;120(2):537-9.

Manoharan et al., Dense packing and symmetry in small clusters of microspheres. Science. Jul. 25, 2003;301:483-87.

Marques et al., Porous Flow within Concentric Cylinders. Bulletin of the American Physical Society Division of Fluid Dynamics. Nov. 1996;41:1768. Available at http://flux.aps.org/meetings/YR9596/BAPSDFD96/abs/G1070001.html (downloaded Oct. 11, 2006) 2 pages.

Melin et al., A liquid-triggered liquid microvalve for on-chip flow control. Sensors and Actuators B. May 2004;100(3):463-68.

Mock et al., Synthesis of anisotropic nanoparticles by seeded emulsion polymerization. Langmuir. Apr. 25, 2006;22(9):4037-43. Published on web Mar. 31, 2006.

Naka et al., Control of crystal nucleation and growth of calcium carbonate bysynthetic substrates. Chem Mater 2001;13:3245-59.

Nakano et al., Single-molecule PCR using water-in-oil emulsion. J Biotechnol. Apr. 24, 2003;102(2):117-24.

Nie et al., Polymer particles with various shapes and morphologies produced in continuous microfluidic reactors. J Am Chem Soc. Jun. 8, 2005;127(22):8058-63.

Nihant et al., Polylactide microparticles prepared by double emulsion/evaporation technique. I. Effect of primary emulsion stability. Pharm Res. Oct. 1994;11(10):1479-84.

Nikolaides et al., Two Dimensional Crystallisation on Curved Surfaces. MRS Fall 2000 Meeting. Boston, MA. Nov. 27, 2000. Abstract #41061.

Nisisako et al., Controlled formulation of monodisperse double emulsions in a multiple-phase microfluidic system. Soft Matter. 2005;1:23-7. Month not cited on publication.

Nisisako, Microstructured Devices for Preparing Controlled Multiple Emulsions. Chem Eng Technol. 2008;31:1091-8. Month not cited on publication.

Nof et al., Drug-releasing scaffolds fabricated from drug-loaded microspheres. J Biomed Mater Res. Feb. 2002;59(2):349-56.

Oh et al., Distribution of macropores in silica particles prepared by using multiple emulsions. J Colloid Interface Sci. Oct. 1, 2002;254(1):79-86.

Okubo et al., Micron-sized, monodisperse, snowman/confetti-shaped polymer particles by seeded dispersion polymerization. Colloid Polym. Sci. 2005;283:1041-45. Published online Apr. 2, 2005.

Pannacci et al., Equilibrium and nonequilibrium states in microfluidic double emulsions. Phys Rev Lett. Oct. 17, 2008;101(16):164502. Epub Oct. 14, 2008. 4 pages.

Perez et al., Poly(lactic acid)-poly(ethylene glycol) nanoparticles as new carriers for the delivery of plasmid DNA. Journal of Controlled Release. 2001;75:211-224. Month not cited on publication.

Piemi et al., Transdermal delivery of glucose through hairless rat skin in vitro: effect of multiple and simple emulsions. Int J Pharm. 1998; 171:207-15. Month not cited on publication.

Priest et al., Generation of monodisperse gel emulsions in a microfluidic device. App Phys Lett. 2006;88:024106. 3 pages. Published online Jan. 12, 2006.

Quevedo et al., Interfacial polymerization within a simplified microfluidic device: capturing capsules. J Am Chem Soc. Aug. 3, 2005;127(30):10498-9.

Raghuraman et al., Emulsion liquid membranes for wastewater treatment: equilibrium models for some typical metal-extractant systems. Environ Sci Technol. Jun. 1, 1994;28(6):1090-8.

Reculusa et al., Synthesis of daisy-shaped and multipod-like silica/polystyrene nanocomposites. Nano Lett. 2004;4:1677-82. Published on web Jul. 14, 2004.

(56) References Cited

OTHER PUBLICATIONS

Roh et al., Biphasic janus particles with nanoscale anisotropy. Nature Med. Oct. 2005;4:759-63.
Rojas et al., Induction of instability in water-in-oil-in-water double emulsions by freeze-thaw cycling. Langmuir. Jun. 19, 2007;23(13):6911-7. Epub May 24, 2007.
Rojas et al., Temperature-induced protein release from water-in-oil-in-water double emulsions. Langmuir. Jul. 15, 2008;24(14):7154-60. Epub Jun. 11, 2008.
Schubert et al., Designer Capsules. Nat Med. Dec. 2002;8:1362.
Seo et al., Microfluidic consecutive flow-focusing droplet generators. Soft Matter. 2007;3:986-92. Published online May 29, 2007.
Sheu et al., Phase separation in polystyrene latex interpenetrating polymer networks. J. Poly. Sci. A. Poly. Chem. 1990;28:629-51. Month not cited on publication.
Shum et al., Abstract: P9.00001 : Microfluidic Fabrication of Bio-compatible Vesicles by Self-assembly in Double Emulsions. 2008 APS March Meeting. Mar. 10-14, 2008. New Orleans, LA. Submitted Nov. 26, 2007. Presented Mar. 12, 2008. Abstract Only.
Shum et al., Double emulsion templated monodisperse phospholipid vesicles. Langmuir. Aug. 5, 2008;24(15):7651-3. Epub Jul. 10, 2008.
Shum et al., Microfluidic Fabrication of Bio-compatible Vesicles Using Double Emulsion Drops as Templates. APS March Meeting 2008. Presented Mar. 12, 2008. 16 pages.
Shum et al., Microfluidic fabrication of monodisperse biocompatible and biodegradable polymersomes with controlled permeability. J Am Chem Soc. Jul. 23, 2008;130(29):9543-9. Epub Jun. 25, 2008.
Shum et al., Template-Directed Assembly of Amphiphiles in Controlled Emulsions by Microfluidics. $82^{nd}$ ACS Colloid & Surface Science Symposium. Jun. 15-18, 2008. Presented Jun. 16, 2008. Abstract Only.
Silva-Cunha et al., W/O/W multiple emulsions of insulin containing a protease inhibitor and an absorption enhancer: biological activity after oral administration to normal and diabetic rats. Int J Pharmaceutics. 1998;169:33-44. Month not cited on publication.
Sim et al. The shape of a step structure as a design aspect to control droplet generation in microfluidics. J Micromech Microeng. Feb. 9, 2010;20:035010. 6 pages.
Skjeltorp et al., Preparation of nonspherical, monodisperse polymer particles and their self-organization. J. Colloid Interf. Sci. Oct. 1986;113:577-82.
Sohn et al., Capacitance cytometry: measuring biological cells one by one. Proc Natl Acad Sci U S A. Sep. 26, 2000;97(20):10687-90.
Song et al., A microfluidic system for controlling reaction networks in time. Angew Chem Int Ed Engl. Feb. 17, 2003;42(7):768-72.
Sun et al., Microfluidic melt emulsification for encapsulation and release of actives. ACS Appl Mater Interfaces. Dec. 2010;2(12):3411-6. Epub Nov. 17, 2010.
Takeuchi et al., An Axisymmetric Flow-Focusing Microfluidic Device. Adv Mater. Apr. 18, 2005;17:1067-72.
Tan et al., Controlled Fission of Droplet Emulsions in Bifurcating Microfluidic Channel. Boston. Transducers. 2003. 4 pages. Month not cited on publication.
Tan et al., Design of microfluidic channel geometries for the control of droplet volume, chemical concentration, and sorting. Lab Chip. Aug. 2004;4(4):292-8. Epub Jul. 1, 2004.
Tan, Monodisperse Droplet Emulsions in Co-Flow Microfluidic Channels. Lake Tahoe. Micro TAS. 2003. 2 pages.
Tawfik et al., Man-made cell-like compartments for molecular evolution. Nat Biotechnol. Jul. 1998;16(7):652-6.
Terray et al., Fabrication of linear colloidal structures for microfluidic applications. App Phys Lett. Aug. 26, 2002;81:1555-7.
Terray et al., Microfluidic control using colloidal devices. Science. Jun. 7, 2002;296(5574):1841-4.
Thomas et al., Using a liquid emulsion membrane system for the encapsulation of organic and inorganic substrates within inorganic microcapsules. Chem Commun (Camb). May 21, 2002;(10):1072-3.
Thorsen et al., Dynamic pattern formation in a vesicle-generating microfluidic device. Phys Rev Lett. Apr. 30, 2001;86(18):4163-6.
Ulrich, Chapter 1. General Introduction. Chem. Tech. Carbodiimides. 2007:1-7. Month not cited on publication.
Umbanhowar et al., Monodisperse Emulsion Generation via Drop Break Off in a Coflowing Stream. Langmuir. 2000;16:347-51. Published on web Oct. 14, 1999.
Utada et al., Monodisperse double emulsions generated from a microcapillary device. Science. Apr. 22, 2005;308(5721):537-41.
Van Blaaderen, Colloidal molecules and beyond. Science. Jul. 25, 2003;301:470-71.
Van Blaaderen, Colloids get complex. Nature. Feb. 2006;439:545-46.
Velev et al., Assembly of latex particles by using emulsion droplets. 3. Reverse (water in oil) system. Langmuir. 1997;13:1856-59. Month not cited on publication.
Velev et al., Assembly of latex particles using emulsion droplets as templates. 1. Microstructured hollow spheres. Langmuir. 1996;12:2374-84. Month not cited on publication.
Velev et al., Assembly of latex particles using emulsion droplets as templates. 2. Ball-like and composite aggregates. Langmuir. 1996;12:2385-91. Month not cited on publication.
Wang, Fabrication of a Toroidal Structure of Polymer Particle by Phase Separation with One Dimensional Axial Flow in Microchannel . . . $82^{nd}$ ACS Colloid & Surface Science Symposium. Jun. 15-18, 2008. Presented Jun. 17, 2008. Abstract Only.
Weitz, Nonspherical engineering of polymer colloids. Web Page. Exp. Soft Condensed Matter Group. Last updated Nov. 10, 2005. 1 page.
Weitz, Packing in the spheres. Science. Feb. 13, 2004;303:968-969.
Wolff et al., Integrating advanced functionality in a microfabricated high-throughput fluorescent-activated cell sorter. Lab Chip. Feb. 2003;3(1):22-7. Epub Jan. 23, 2003.
Xu et al., Generation of Monodisperse Particles by Using Microfluidics: Control over Size, Shape and Composition. Angew Chem Int Ed. 2004;43:2-5. Month not cited on publication.
Yamaguchi et al., Insulin-loaded biodegradable PLGA microcapsules: initial burst release controlled by hydrophilic additives. J Control Release. Jun. 17, 2002;81(3):235-49.
Yin et al., Template-assisted self-assembly: a practical route to complex aggregates of monodispersed colloids with well-defined sizes, shapes, and structures. JACS. 2001;123:8718-29. Published on web Aug. 15, 2001.
Yoon et al., Abstract: X8.00007 : Fabrication of phospholipid vesicles from double emulsions in microfluidics. 2008 APS March Meeting. Mar. 10-14, 2008. New Orleans, LA. Submitted Nov. 26, 2007. Presented Mar. 14, 2008. Abstract Only.
Yoon et al., Fabrication of giant phospholipid vesicles from double emulsions in microfluidics. APS March Meeting 2008. Presented Mar. 14, 2008. 11 pages.
Zhang et al., A Simple Statistical Parameter for Use in Evaluation and Validation of High Throughput Screening Assays. J Biomol Screen. 1999;4(2):67-73. Month not cited on publication.
Zhao et al., Enhanced encapsulation of actives in self-sealing microcapsules by precipitation in capsule shells. Langmuir. Dec. 6, 2011;27(23):13988-91. Epub Oct. 26, 2011.
Zhao, Preparation of hemoglobin-loaded nano-sized particles with porous structure as oxygen carriers. Biomaterials. 2007;28:1414-1422. Available online Nov. 28, 2006.
Zheng et al., A microfluidic approach for screening submicroliter volumes against multiple reagents by using preformed arrays of nanoliter plugs in a three-phase liquid/liquid/gas flow. Angew Chem Int Ed Engl. Apr. 22, 2005;44(17):2520-3.
Zimmermann et al., Microscale production of hybridomas by hypo-osmolar electrofusion. Hum Antibodies Hybridomas. Jan. 1992;3(1):14-8.
Final Rejection dated Mar. 2, 2018 for Application No. 10-2012-7008201.
International Search Report and Written Opinion dated Nov. 6, 2013 for Application No. PCT/US2012/050916.
Office Communication dated Apr. 1, 2016 for U.S. Appl. No. 14/961,460.
Advisory Action dated Sep. 25, 2014 for U.S. Appl. No. 13/586,628.

(56) References Cited

OTHER PUBLICATIONS

Oh et al., Hydrodynamic micro-encapsulation of aqueous fluids and cells via 'on the fly' photopolymerization. J Micromech and Microeng. Jan. 9, 2006;16(2);285-91.
Okushima et al., Controlled production of monodisperse double emulsions by two-step droplet breakup in microfluidic devices. Langmuir. Nov. 9, 2004;20(23):9905-8.
Ouellette, A New Wave of Microfluidic Device. The Industrial Physicist. Aug./Sep. 2003:14-7.

* cited by examiner

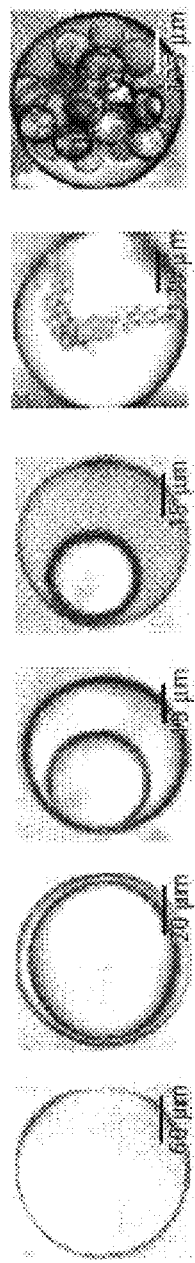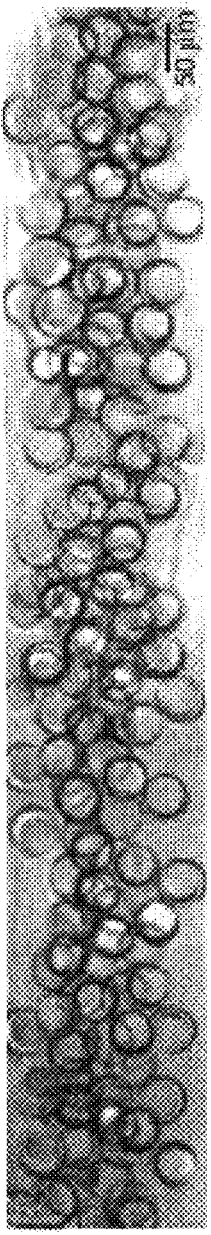

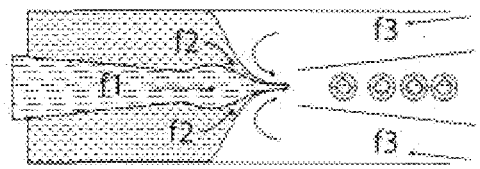 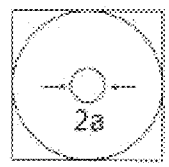
Fig. 7A  Fig. 7B
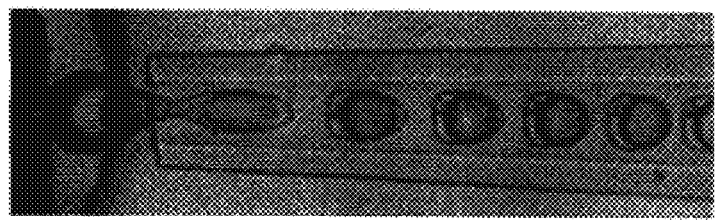
Fig. 8A
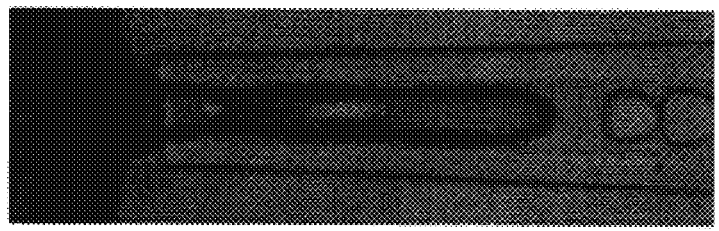
Fig. 8B
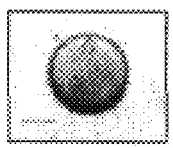 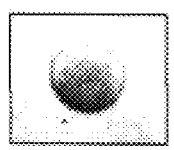 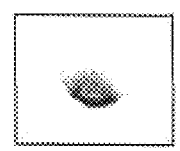 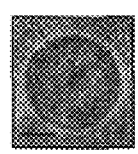
Fig. 9A   Fig. 9B   Fig. 9C   Fig. 9D
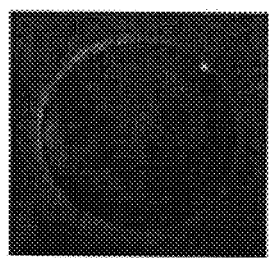 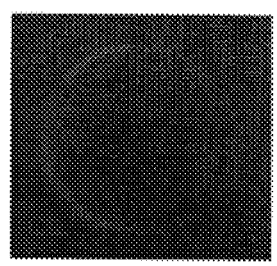
Fig. 10A   Fig. 10B

METHOD AND APPARATUS FOR FORMING MULTIPLE EMULSIONS

RELATED APPLICATIONS

This application is a continuation of U.S. application Ser. No. 11/885,306, having a § 371 date of Oct. 22, 2008, entitled "Methods and Apparatus for Forming Multiple Emulsions," which is a U.S. National Stage Application of International Application No. PCT/US2006/07772, filed Mar. 3, 2006, entitled "Methods and Apparatus for Forming Multiple Emulsions," which claims the benefit of U.S. Provisional Patent Application Ser. No. 60/659,045, filed Mar. 4, 2005, entitled "Methods and Apparatus for Forming Multiple Emulsions," by Waits, et al., each of which are incorporated herein.

GOVERNMENT FUNDING

This invention was made with government support under Grant No. DMR-0243715 awarded by the National Science Foundation. The government has certain rights in the invention.

FIELD OF INVENTION

The present invention relates generally to emulsions and the production of emulsions, and more particularly, to microfluidic systems for forming multiple emulsions, and emulsions produced therefrom.

BACKGROUND

An emulsion is a fluidic state which exists when a first fluid is dispersed in a second fluid that is typically immiscible or substantially immiscible with the first fluid. Examples of common emulsions are oil in water and water in oil emulsions. Multiple emulsions are emulsions that are formed with more than two fluids, or two or more fluids arranged in a more complex manner than a typical two-fluid emulsion. For example, a multiple emulsion may be oil-in-water-in-oil, or water-in-oil-in-water. Multiple emulsions are of particular interest because of current and potential applications in fields such as pharmaceutical delivery, paints and coatings, food and beverage, and health and beauty aids.

Typically, multiple emulsions consisting of a droplet inside another droplet are made using a two-stage emulsification technique, such as by applying shear forces through mixing to reduce the size of droplets formed during the emulsification process. Other methods such as membrane emulsification techniques using, for example, a porous glass membrane, have also been used to produce water-in-oil-in-water emulsions. Microfluidic techniques have also been used to produce droplets inside of droplets using a procedure including two or more steps. For example, see International Patent Application No. PCT/US2004/010903, filed Apr. 9, 2004, entitled "Formation and Control of Fluidic Species," by Link, et al., published as WO 2004/091763 on Oct. 28, 2004; or International Patent Application No. PCT/US03/20542, filed Jun. 30, 2003, entitled "Method and Apparatus for Fluid Dispersion," by Stone, et al., published as WO 2004/002627 on Jan. 8, 2004, each of which is incorporated herein by reference. See also Anna, et al., "Formation of Dispersions using 'Flow Focusing' in Microchannels," *Appl. Phys. Lett.*, 82:364 (2003) and Okushima, et al., "Controlled Production of Monodispersed Emulsions by Two-Step Droplet Breakup in Microfluidic Devices," *Langmuir* 20:9905-9908 (2004). In some of these examples, a T-shaped junction in a microfluidic device is used to first form an aqueous droplet in an oil phase, which is then carried downstream to another T-junction where the aqueous droplet contained in the oil phase is introduced into another aqueous phase. In another technique, co-axial jets can be used to produce coated droplets, but these coated droplets must be re-emulsified into the continuous phase in order to form a multiple emulsion. See Loscertales et al., "Micro/Nano Encapsulation via Electrified Coaxial Liquid Jets," *Science* 295:1695 (2002).

Multiple emulsions and the products that can be made from them can be used to produce a variety of products useful in the food, coatings, cosmetic, or pharmaceutical industries, for example. Methods for producing multiple emulsions providing consistent droplet sizes, consistent droplet counts, consistent coating thicknesses, and/or improved control would make commercial implementation of these products more viable.

SUMMARY OF INVENTION

The subject matter of this application may involve, in some cases, interrelated products, alternative solutions to a particular problem, and/or a plurality of different uses of a single system or article.

In one aspect a method of making a multiple emulsion is provided, the method comprising forming a first droplet from a first fluid stream surrounded by a second fluid while the second fluid is surrounded by a third fluid.

In another aspect a method is provided, the method comprising flowing a first fluid stream in a first direction, flowing a second fluid stream in the same direction as the first fluid, the second stream circumscribing the first stream, flowing a third fluid stream in a second direction that is substantially opposed to the first direction, and altering the direction of flow of the third fluid stream to flow substantially parallel to the first direction.

In another aspect, an apparatus for forming droplets is provided, the apparatus comprising a first conduit having a first diameter a second conduit including an end defining an exit opening, the second conduit concentrically disposed in the first conduit, and a third conduit including an end defining an entrance opening, the third conduit concentrically disposed in the first conduit wherein the entrance opening opposes the exit opening of the second conduit.

In another aspect, a method of packaging a species is provided, the method comprising suspending a species in a first fluid, flowing the first fluid in a stream surrounded by a second fluid stream, the second fluid being substantially immiscible with the first fluid, introducing a third fluid stream that surrounds the second fluid stream, and forming multiple droplets of the first fluid wherein the droplets contain at least one of the species.

In another aspect, a method for forming droplets is provided, the method comprising flowing a first fluid in a first conduit, flowing a second fluid in a second conduit and expelling the second fluid, from an end defining an exit opening of the second conduit, into the first fluid in the first conduit, urging the second fluid, surrounded by the first fluid, into a restriction under conditions in which droplets of the second fluid in the first fluid are formed within the restriction, and releasing the droplets of the second fluid carried in the first fluid from the restriction into a region of dimension larger than the restriction.

In yet another aspect, a method for forming droplets is provided, the method comprising flowing a first fluid in a first conduit, flowing a second fluid in a second conduit and expelling the second fluid, from an end defining an exit opening of the second conduit, into the first fluid in the first conduit, flowing a third fluid in a third conduit and expelling the third fluid, from an end defining an exit opening of the third conduit, into the second fluid in the second conduit, urging the second fluid, surrounded by the first fluid and containing the third fluid, into a restriction under conditions in which droplets of the second fluid in the first fluid are formed within the restriction, and releasing the droplets of the second fluid carried in the first fluid from the restriction into a region of dimension larger than the restriction.

In one aspect, the present invention provides a colloidosome having at least a first particle shell and a second particle shell surrounding the first particle shell.

In another aspect, the present invention provides a liposome comprising a lipid bilayer having an inner lipid layer and an outer lipid layer. In some embodiments, the inner lipid layer comprises a first lipid composition and the outer lipid layer comprises a second lipid composition distinguishable from the first lipid composition.

In yet another aspect, the present invention provides an inner fluid, a first middle fluid surrounding the inner fluid, a second middle fluid surrounding the first middle fluid, and an outer liquid surrounding the second middle fluid.

In another aspect, the present invention is directed to a method of making one or more of the embodiments described herein. In another aspect, the present invention is directed to a method of using one or more of the embodiments described herein.

Other advantages, features, and uses of the invention will become apparent from the following detailed description of non-limiting embodiments of the invention when considered in conjunction with the accompanying drawings, which are schematic and which are not intended to be drawn to scale. In the figures, each identical or nearly identical component that is illustrated in various figures typically is represented by a single numeral. For purposes of clarity, not every component is labeled in every figure, nor is every component of each embodiment of the invention shown where illustration is not necessary to allow those of ordinary skill in the art to understand the invention. In cases where the present specification and a document incorporated by reference include conflicting disclosure, the present specification shall control.

BRIEF DESCRIPTION OF DRAWINGS

Non-limiting embodiments of the present invention will be described by way of example with reference to the accompanying figures, which are schematic and are not intended to be drawn to scale. In the figures, each identical or nearly identical component illustrated is typically represented by a single numeral. For purposes of clarity, not every component is labeled in every figure, nor is every component of each embodiment of the invention shown where illustration is not necessary to allow those of ordinary skill in the art to understand the invention. In the figures:

FIGS. 2A-2G are copies of photomicrographs showing different multiple emulsions, another embodiment of the invention;

FIGS. 7A-7B are schematic illustrations of a microfluidic device according to another embodiment of the invention;

FIGS. 8A-8B are copies of photomicrographs illustrating the influence of diblock copolymers on multiple emulsions, in another embodiment of the invention;

FIGS. 9A-9D illustrate evaporation and dissolution of a THF-toluene mixture, in accordance with another embodiment of the invention;

FIGS. 10A-10B illustrate the encapsulation of hydrophobic quantum dots, in still another embodiment of the invention;

DETAILED DESCRIPTION

Figure 1:
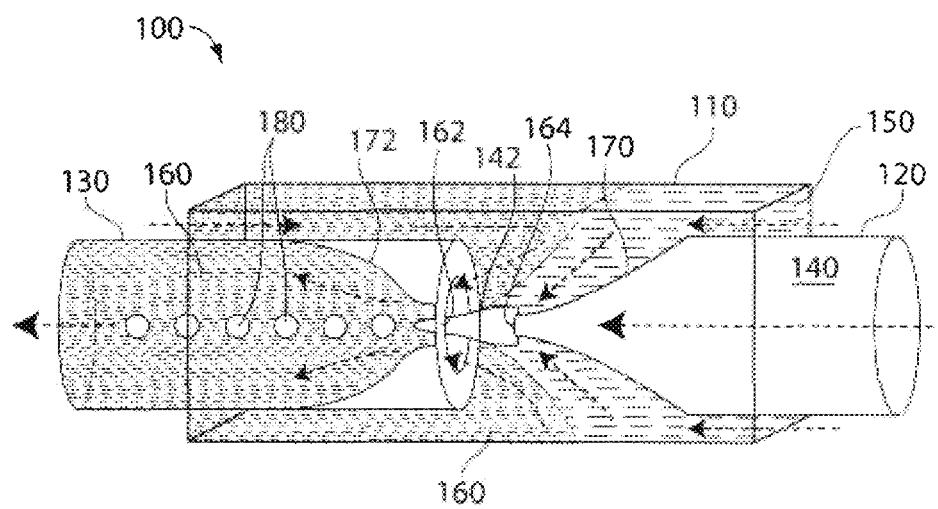
FIG. 1 is a schematic illustration of a microfluidic device useful in making multiple emulsions, according to one embodiment of the invention.

The present invention generally relates to multiple emulsions, and to methods and apparatuses for making multiple emulsions. A multiple emulsion, as used herein, describes larger droplets that contain one or more smaller droplets therein. The larger droplet or droplets may be suspended in a third fluid in some cases. In certain embodiments, emulsion degrees of nesting within the multiple emulsion are possible. For example, an emulsion may contain droplets containing smaller droplets therein, where at least some of the smaller droplets contain even smaller droplets therein, etc. Multiple emulsions can be useful for encapsulating species such as pharmaceutical agents, cells, chemicals, or the like. In some cases, one or more of the droplets (e.g., an inner droplet and/or an outer droplet) can change form, for instance, to become solidified to form a microcapsule, a liposome, a polymerosome, or a colloidosome. As described below, multiple emulsions can be formed in one step in certain embodiments, with generally precise repeatability, and can be tailored to include one, two, three, or more inner droplets within a single outer droplet (which droplets may all be nested in some cases). As used herein, the term "fluid" generally means a material in a liquid or gaseous state. Fluids, however, may also contain solids, such as suspended or colloidal particles.

Fields in which multiple emulsions may prove useful include, for example, food, beverage, health and beauty aids, paints and coatings, and drugs and drug delivery. For instance, a precise quantity of a drug, pharmaceutical, or other agent can be encapsulated by a shell designed to rupture under particular physiological conditions. In some instances, cells can be contained within a droplet, and the cells can be stored and/or delivered, e.g., via a polymerosome. Other species that can be stored and/or delivered include, for example, biochemical species such as nucleic acids such as siRNA, RNAi and DNA, proteins, peptides, or enzymes. Additional species that can be incorporated within a multiple emulsion of the invention include, but are not limited to, nanoparticles, quantum dots, fragrances, proteins, indicators, dyes, fluorescent species, chemicals, or the like. A multiple emulsion can also serve as a reaction vessel in certain cases, such as for controlling chemical reactions, or for in vitro transcription and translation, e.g., for directed evolution technology.

Using the methods and devices described herein, in some embodiments, a consistent size and/or number of droplets can be produced, and/or a consistent ratio of size and/or number of outer droplets to inner droplets (or other such ratios) can be produced. For example, in some cases, a single droplet within an outer droplet of predictable size can be used to provide a specific quantity of a drug. In addition, combinations of compounds or drugs may be stored, transported, or delivered in a multiple emulsion droplet. For instance, hydrophobic and hydrophilic species can be delivered in a single, multiple emulsion droplet, as the droplet can include both hydrophilic and hydrophobic portions. The amount and concentration of each of these portions can be consistently controlled according to certain embodiments of the invention, which can provide for a predictable and consistent ratio of two or more species in the multiple emulsion droplet.

In one aspect, the multiple emulsions described herein may be made in a single step using different fluids. In one set of embodiments, a triple emulsion may be produced, i.e., an emulsion containing a first fluid, surrounded by a second fluid, which in turn is surrounded by a third fluid. In some cases, the third fluid and the first fluid may be the same. These fluids can be referred to as an inner fluid (IF), a middle fluid (MF) and an outer fluid (OF), respectively, and are often of varying miscibilities due to differences in hydrophobicity. For example, the inner fluid may be water soluble, the middle fluid oil soluble, and the outer fluid water soluble. This arrangement is often referred to as a w/o/w multiple emulsion ("water/oil/water"). Another multiple emulsion may include an inner fluid that is oil soluble, a middle fluid that is water soluble, and an outer fluid that is oil soluble. This type of multiple emulsion is often referred to as an o/w/o multiple emulsion ("oil/water/oil"). It should be noted that the term "oil" in the above terminology merely refers to a fluid that is generally more hydrophobic and not miscible in water, as is known in the art. Thus, the oil may be a hydrocarbon in some embodiments, but in other embodiments, the oil may comprise other hydrophobic fluids.

As used herein, two fluids are immiscible, or not miscible, with each other when one is not soluble in the other to a level of at least 10% by weight at the temperature and under the conditions at which the multiple emulsion is produced. For instance, the fluid and the liquid may be selected to be immiscible within the time frame of the formation of the fluidic droplets. In some embodiments, the inner and outer fluids are compatible, or miscible, while the middle fluid is incompatible or immiscible with each of the inner and outer fluids. In other embodiments, however, all three fluids may be mutually immiscible, and in certain cases, all of the fluids do not all necessarily have to be water soluble. In still other embodiments, additional fourth, fifth, sixth, etc. fluids may be added to produce increasingly complex droplets within droplets, e.g., a first fluid may be surrounded by a second fluid, which may in turn be surrounded by a third fluid, which in turn may be surrounded by a fourth fluid, etc.

In the descriptions herein, multiple emulsions are generally described with reference to a three phase system, i.e., having an outer fluid, a middle fluid, and an inner fluid. However, it should be noted that this is by way of example only, and that in other systems, additional fluids may be present within the multiple droplet. As examples, an emulsion may contain a first fluid droplet and a second fluid droplet, each surrounded by a third fluid, which is in turn surrounded by a fourth fluid; or an emulsion may contain multiple emulsions with higher degrees of nesting. Accordingly, it should be understood that the descriptions of the inner fluid, middle fluid, and outer fluid are by ways of ease of presentation, and that the descriptions below are readily extendable to systems involving additional fluids.

As fluid viscosity can affect droplet formation, in some cases the viscosity of the inner, middle, and/or outer fluids may be adjusted by adding or removing components, such as diluents, that can aid in adjusting viscosity. In some embodiments, the viscosity of the inner fluid and the middle fluid are equal or substantially equal. This may aid in, for example, an equivalent frequency or rate of droplet formation in the inner and middle fluids. In other embodiments, the outer fluid may exhibit a viscosity that is substantially different from either the inner or middle fluids. A substantial difference in viscosity means that the difference in viscosity between the two fluids can be measured on a statistically significant basis. Other distributions of fluid viscosities within the droplets are also possible. For example, the inner fluid may have a viscosity greater than or less than the viscosity of the middle fluid, the middle fluid may have a viscosity that is greater than or less than the viscosity of the outer fluid, etc. It should also be noted that, in higher-order droplets, e.g., containing four, five, six, or more fluids, the viscosities may also be independently selected as desired, depending on the particular application.

In one set of embodiments, multiple emulsions are formed by flowing three (or more) fluids through a system of conduits. The system may be a microfluidic system. "Microfluidic," as used herein, refers to a device, apparatus or system including at least one fluid channel having a cross-sectional dimension of less than about 1 millimeter (mm), and in some cases, a ratio of length to largest cross-sectional dimension of at least 3:1. One or more conduits of the system may be a capillary tube. In some cases, multiple conduits are provided, and in some embodiments, at least some are nested, as described herein. The conduits may be in the microfluidic size range and may have, for example, average inner diameters, or portions having an inner diameter, of less than about 1 millimeter, less than about 300 micrometers, less than about 100 micrometers, less than about 30 micrometers, less than about 10 micrometers, less than about 3 micrometers, or less than about 1 micrometer, thereby providing droplets having comparable average diameters. One or more of the conduits may (but not necessarily), in cross section, have a height that is substantially the same as a width at the same point. Conduits may include an orifice that may be smaller, larger, or the same size as the average diameter of the conduit. For example, conduit orifices may have diameters of less than about 1 mm, less than about 500 micrometers, less than about 300 micrometers, less than about 200 micrometers, less than about 100 micrometers, less than about 50 micrometers, less than about 30 micrometers, less than about 20 micrometers, less than about 10 micrometers, less than about 3 micrometers, etc. In cross-section, the conduits may be rectangular or substantially non-rectangular, such as circular or elliptical. The conduits of the present invention can also be disposed in or nested in another conduit, and multiple nestings are possible in some cases. In some embodiments, one conduit can be concentrically retained in another conduit and the two conduits are considered to be concentric. In other embodiments, however, one conduit may be off-center with respect to another, surrounding conduit. By using a concentric or nesting geometry, the inner and outer fluids, which are typically miscible, may avoid contact facilitating great flexibility in making multiple emulsions and in devising techniques for encapsulation and polymerosome formation. For example, this technique allows for fabrication of core-shell structure, and these core-shell structures can be converted into capsules.

As the systems described herein may be truly three-dimensional microfluidic devices, e.g., having concentric conduit arrangements, the inner fluid can be completely shielded from the outer fluid in certain embodiments. This may reduce or eliminate problems that can occur in other systems, when the inner and outer fluid may contact each other at or near a solid surface, such as in a two-dimensional system.

A flow pathway can exist in an inner conduit and a second flow pathway can be formed in a coaxial space between the external wall of the interior conduit and the internal wall of the exterior conduit, as discussed in detail below. The two conduits may be of different cross-sectional shapes in some cases. In one embodiment, a portion or portions of an interior conduit may be in contact with a portion or portions of an exterior conduit, while still maintaining a flow pathway in the coaxial space. Different conduits used within the same device may be made of similar or different materials. For example, all of the conduits within a specific device may be glass capillaries, or all of the conduits within a device may be formed of a polymer, for example, polydimethylsiloxane, as discussed below.

A geometry that provides coaxial flow can also provide hydrodynamic focusing of that flow, according to certain embodiments of the invention. Many parameters of the droplets, both inner droplets and middle layer droplets (outer droplets) can be controlled using hydrodynamic focusing. For instance, droplet diameter, outer droplet thickness and the total number of inner droplets per outer droplet can be controlled.

Multiple emulsion parameters can also be engineered by adjusting, for example, the system geometry, the flowrate of the inner fluid, the flowrate of the middle fluid and/or the flowrate of the outer fluid. By controlling these three flow rates independently, the number of internal droplets and the shell thickness of the outer droplet (middle fluid) can be predicatively chosen.

The schematic diagram illustrated in FIG. 1 shows one embodiment of the invention including a device 100 having an outer conduit 110, a first inner conduit (or injection tube) 120, and a second inner conduit (or collection tube) 130. An inner fluid 140 is shown flowing in a right to left direction and middle fluid 150 flows in a right to left direction in the space outside of injection tube 120 and within conduit 110. Outer fluid 160 flows in a left to right direction in the pathway provided between outer conduit 110 and collection tube 130. After outer fluid 160 contacts middle fluid 150, it changes direction and starts to flow in substantially the same direction as the inner fluid 140 and the middle fluid 150, right to left. Injection tube 120 includes an exit orifice 164 at the end of tapered portion 170. Collection tube 130 includes an entrance orifice 162, an internally tapered surface 172, and exit channel 168. Thus, the inner diameter of injection tube 120 decreases in a direction from right to left, as shown, and the inner diameter of collection tube 130 increases from the entrance orifice in a direction from right to left. These constrictions, or tapers, can provide geometries that aid in producing consistent multiple emulsions. The rate of constriction may be linear or non-linear.

As illustrated in FIG. 1, inner fluid 140 exiting from orifice 164 can be completely surrounded by middle fluid 150, as there is no portion of inner fluid 140 that contacts the inner surface of conduit 110 after its exit from injection tube 120. Thus, for a portion between exit orifice 164 to a point inside of collection tube 130 (to the left of entrance orifice 162), a stream of fluid 140 is concentrically surrounded by a stream of fluid 150. Additionally, middle fluid 150 may not come into contact with the surface of collection tube 130, at least until after the multiple emulsion has been formed, because it is concentrically surrounded by outer fluid 160 as it enters collection tube 130. Thus, from a point to the left of exit orifice 164 to a point inside of collection tube 130, a composite stream of three fluid streams is formed, including inner fluid 140 concentrically surrounded by a stream of middle fluid 150, which in turn is concentrically surrounded by a stream of outer fluid 160. The inner and middle fluids do not typically break into droplets until they are inside of collection tube 130 (to the left of entrance orifice 162). Under "dripping" conditions, the droplets are formed closer to the orifice, while under "jetting" conditions, the droplets are formed further downstream, i.e., to the left as shown in FIG. 1.

In some cases, such as when droplets of middle fluid 150 (outer droplets) are formed at the same rate as are droplets of inner fluid 140, then there is a one-to-one correspondence between inner fluid and middle fluid droplets, and each droplet of inner fluid is surrounded by a droplet of middle fluid, and each droplet of middle fluid contains a single inner droplet of inner fluid. The term "outer droplet," as used herein, typically means a fluid droplet containing an inner fluid droplet that comprises a different fluid. In many embodiments that use three fluids for multiple emulsion production, the outer droplet is formed from a middle fluid and not from the outer fluid as the term may imply. It should be noted that the above-described figure is by way of example only, and other devices are also contemplated within the instant invention. For example, the device in FIG. 1 may be modified to include additional concentric tubes, for example, to produce more highly nested droplets. For instance, in FIG. 17, a device having three concentric tubes is shown, which may be used to produce nested fluidic droplets having an inner fluid, a first middle fluid surrounding the inner fluid, and a second inner fluid surrounding the first middle fluid. Even higher degrees of nesting are possible, for example, 4 concentric tubes, 5 concentric tubes, or the like. It should be noted that "concentric," as used herein, does not necessarily refer to tubes that strictly coaxial, but also includes nested or "off-center" tubes that do not share a common center line.

Droplet formation and morphology can be affected in a number of ways. For example, the geometry of the device, including the relationship of an outer conduit and two inner conduits, can be useful in developing multiple emulsions of desired size, frequency, and content. For example, the size of the orifice 162 and the inner taper of collection tube 130 can help to maintain three fluids in position, allowing droplets 180 to form. In addition, droplet formation can be affected by the rate of flow of the inner fluid, the rate of flow of the middle fluid, the rate of flow of the outer fluid, the total amount of flow or a change in the ratios, and/or combinations of any of these flow rates. In some embodiments, multiple droplets of inner fluid can be formed within a single droplet of the middle fluid. For example, 2, 3, 4, 5, 10, 30, 100, 300, 1000 or more droplets of inner fluid can be formed within a droplet of middle fluid by varying the frequency of droplet formation of either (or both) the inner fluid or the middle fluid, in relation to the other of the inner fluid or the middle fluid. For example, if the velocity of the inner fluid is altered so that five droplets are formed over the same amount of time as a single droplet of middle fluid, then a droplet of middle fluid may contain, on average, five droplets of inner fluid. It should be noted that, depending on the fluid flow characteristics, some of the middle fluid droplets may contain more or fewer droplets of inner fluid, although the average is five droplets, as discussed in this example. As the absolute and relative flow rates of the three fluids can be carefully controlled using the devices described herein, the middle fluid droplets containing specific numbers of inner fluid droplets can be consistently and repeatedly formed. In some embodiments, the standard deviation from a target number of inner fluid droplets per middle fluid droplet may be, for example, less than one inner droplet, or less than 20% of the number of inner droplets per middle fluid droplet. In other embodiments, the standard deviation may be, for example, less than 15%, less than 12%, less than 10%, less than 8%, or less than 6% of the number of inner droplets per middle fluid droplet.

Dripping conditions produce droplets close to the entrance of collection tube 130 (FIG. 1) within a single orifice diameter; this can be analogized to a dripping faucet. Droplets produced by dripping are typically highly monodisperse. By contrast, under jetting conditions, as illustrated in FIG. 3B, produces a long jet that extends three or more orifice diameters downstream into the collection tube, where it breaks into droplets. Although the distance from the opening may be greater under the jetting regime, droplets formed by either method are typically formed inside the collection tube. The jetting regime is typically quite irregular, resulting in polydisperse droplets, whose radius is much greater than that of the jet. Jet formation is believed to be caused by the viscous stress of the outer fluid on the middle fluid. When viscous effects dominate over inertial effects, the Reynolds number is low. The formation of multiple emulsions is similar to that of single emulsions; however, there are at least two fluids flowing coaxially, each of which can form droplets through either mechanism.

The size distribution of the multiple emulsions is believed to be determined by the breakup mechanism, whereas the number of innermost droplets (inner fluid) may depend on the relative rates of droplet formation of the inner and middle fluids. As a result, a wide variety of droplet morphologies can be produced. For example, FIGS. 5A-5F, shows different sized mono- and polydisperse multiple emulsions. When the rates of breakup and formation are equal, the annulus and core of the coaxial jet can break simultaneously, which can be used to generate a multiple emulsion with a single internal drop. These types of multiple emulsions can be generated when both fluids are simultaneously dripping (FIG. 3A) or simultaneously jetting (FIG. 3B). The dripping and jetting mechanisms are closely related, and the transition between them can be induced by varying the flowrate of the outermost fluid. The dripping regime occurs at lower outer flow rates, while increasing the flowrate focuses the coaxial jet more strongly, thinning the inner stream, leading initially to smaller multiple emulsion droplets.

The relative sizes of the inner fluid droplet and the middle fluid droplet can also be carefully controlled, i.e., the ratio of the size of the inner and outer droplets can be predicatively controlled. For instance, inner fluid droplets may fill much of or only a small portion of the middle fluid (outer) droplet. Inner fluid droplets may fill less than 90%, less than 80%, less than 70%, less than 60%, less than 50%, less than 30%, less than 20%, or less than 10% of the volume of the outer droplet. Alternatively, the inner fluid droplet may form greater than 10%, 20%, 30%, 40%, 50%, 60%, 70%, 90%, 95%, or 99% of the volume of the outer droplet. In some cases, the outer droplet can be considered a fluid shell, or coating, when it contains an inner droplet, as some or most of the outer droplet volume may be filled by the inner droplet. The ratio of the middle fluid shell thickness to the middle fluid droplet radius can be equal to or less than, e.g., 5%, 4%, 3%, or 2%. This can allow, in some embodiments, for the formation of multiple emulsions with only a very thin layer of material separating, and thus stabilizing, two miscible fluids. The middle shell material can also be thickened to greater than or equal to, e.g., 10%, 20%, 30%, 40%, or 50% of the middle fluid droplet radius. Examples of different size inner droplets with a constant sized outer droplet are provided in FIGS. 2A-2D. For example, FIGS. 2E and 2F illustrate a single middle fluid droplet containing a plurality of inner fluid droplets.

Figure 3A:
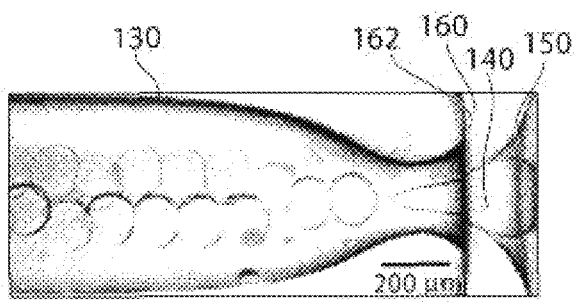
FIGS. 3A and 3B are copies of photomicrographs illustrating formation of droplets in the dripping (A) and jetting (B) regimes, in accordance with yet another embodiment of the invention.
Figure 3B:
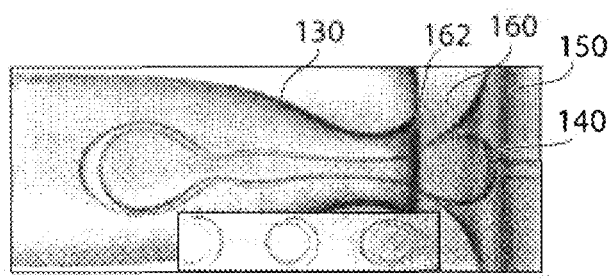

FIG. 3 provides two photomicrographs showing the formation of monodisperse droplets in the dripping region (FIG. 3A) and in the jetting region (FIG. 3B). In both cases, monodisperse droplets are formed downstream of the entrance orifice to collection tube 130. However, it is notable that droplets break off more closely to the entrance orifice when the system is operated in the dripping region than when the system is operated under jetting conditions. In the example shown, using the same device, a change in the flow of the outer fluid can be used to control whether jetting or dripping action is employed. In this example, the dripping region resulted in a polydispersity of less than about 1%, while in the jetting region, polydisperity was about 3%. The scale bar shown in FIG. 3A represents 200 micrometers. In both examples, the outer fluid and the inner fluid were silicon oil and the middle fluid was a glycerol/water mixture. The inner fluid and middle fluid were of substantially equal viscosities, and the outer fluid exhibited a viscosity of about 1 order of magnitude greater than the viscosity of either the inner or middle fluid.

Figure 17:
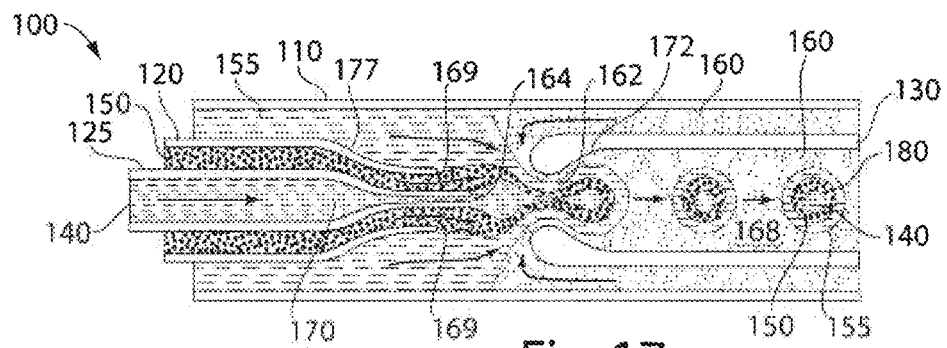
FIG. 17 is a schematic illustration of another microfluidic device useful in making multiple emulsions, according to another embodiment of the invention.

As noted above, the invention also provides, in certain aspects, triple emulsions or other, higher-order multiple emulsions. For example, in FIG. 17, an apparatus for producing triple emulsions is illustrated. In FIG. 17, device 100 has an outer conduit 110, a first inner conduit (or injection tube) 120, a second inner conduit (or injection tube) 125, and a third inner conduit (or collection tube) 130. An inner fluid 140 is shown flowing in a left to right direction within conduit 125, as well as first middle fluid 150 within the space outside of conduit 125 and within conduit 120. Second middle fluid 155 also flows in a left to right direction in FIG. 17, outside of conduit 120 and within conduit 110. Outer fluid 160 flows in a right to left direction in the pathway provided between outer conduit 110 and collection tube 130. After outer fluid 160 contacts second middle fluid 155, it changes direction and starts to flow in substantially the same direction as inner fluid 140 and middle fluids 150 and 155, i.e., left to right. Through this action, a series of nested emulsions 180 are formed, in which inner fluid 140 is surrounded by first middle fluid 150, which in turn surround by second middle fluid 155, which in contained within outer fluid 160. Injection tube 125 includes an exit orifice 164 at the end of tapered portion 170, while injection tube 125 includes an exit orifice 169 at the end of tapered portion 177. Collection tube 130 includes an entrance orifice 162 and an internally tapered surface 172, as well as exit 168. The inner diameter of injection tube 120 generally decreases in a direction from left to right, as shown, the inner diameter of injection tube 125 also decreases in the direction from left to right, as shown, in the inner diameter of collection tube 130 increase from the entrance orifice in a direction from left to right. These constrictions, or tapers can provide geometries that aid in producing consistent multiple emulsions.

Figure 18A:
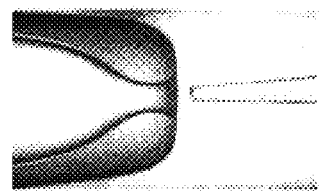
FIGS. 18A-18G are copies of photomicrographs showing various multiple emulsions, according to various embodiments of the invention.
Figure 18B:
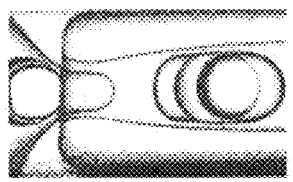
Figure 18C:
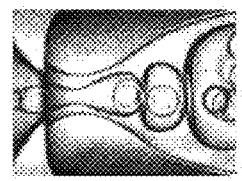
Figure 18D:
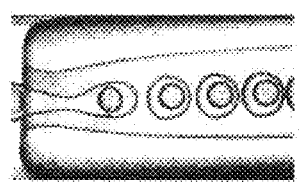
Figure 18E:
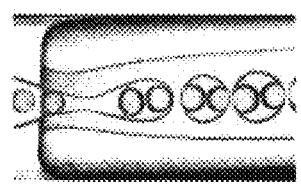
Figure 18F:
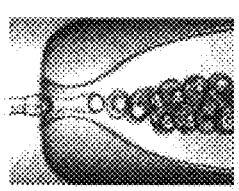
Figure 18G:
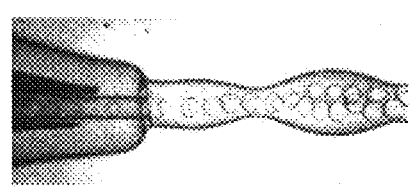

Examples of such multiple emulsions are illustrated in FIGS. 18A-18G. FIG. 18A illustrates an example of a device that was used to produce the multiple emulsions shown in FIGS. 18B-18G. In FIG. 18A, the dimension of the tips is on the order of 100 mm. FIGS. 18B-18D illustrate various water/oil/water/oil ("w/o/w/o") emulsions. In FIG. 18B, a water/silicon oil/water/silicon oil emulsion is shown, while in FIG. 18C, a water/toluene/water/silicon oil emulsion is shown. As noted above, the volume of each component within a multiple emulsion can be tuned by controlling the various flow rates, and in some cases, multiple droplets may be contained within a single droplet. For instance, in FIG. 18E, within the fluidic droplets are contained to distinct inner fluidic droplets, while in FIGS. 18F and 18G, several inner fluidic droplets are contained within an outer fluidic droplet.

The rate of production of multiple emulsion droplets may be determined by the droplet formation frequency, which under many conditions can vary between approximately 100 Hz and 5000 Hz. In some cases, the rate of droplet production may be at least about 200 Hz, at least about 300 Hz, at least about 500 Hz, at least about 750 Hz, at least about 1,000 Hz, at least about 2,000 Hz, at least about 3,000 Hz, at least about 4,000 Hz, or at least about 5,000 Hz.

Production of large quantities of multiple emulsion products, e.g., polymerosomes or colloidosomes, can be facilitated by the parallel use of multiple devices in some instances. In some cases, relatively large numbers of devices may be used in parallel, for example at least about 10 devices, at least about 30 devices, at least about 50 devices, at least about 75 devices, at least about 100 devices, at least about 200 devices, at least about 300 devices, at least about 500 devices, at least about 750 devices, or at least about 1,000 devices or more may be operated in parallel. The devices may comprise different conduits (e.g., concentric conduits), orifices, microfluidics, etc. In some cases, an array of such devices may be formed by stacking the devices horizontally and/or vertically. The devices may be commonly controlled, or separately controlled, and can be provided with common or separate sources of inner, middle, and outer fluids, depending on the application.

In some embodiments of the invention, a hardened shell may be formed around an inner droplet, such as by using a middle fluid that can be solidified or gelled. In this way, capsules can be formed with consistently and repeatedly-sized inner droplets, as well as a consistent and repeatedly-sized outer shell. In some embodiments, this can be accomplished by a phase change in the middle fluid. A "phase change" fluid is a fluid that can change phases, e.g., from a liquid to a solid. A phase change can be initiated by a temperature change, for instance, and in some cases the phase change is reversible. For example, a wax or gel may be used as a middle fluid at a temperature which maintains the wax or gel as a fluid. Upon cooling, the wax or gel can form a solid or semisolid shell, e.g., resulting in a capsule. The shell may also be a bilayer, such as can be formed from two layers of surfactant.

In another embodiment, the shell can be formed by polymerizing the middle fluid droplet. This can be accomplished in a number of ways, including using a pre-polymer that can be catalyzed, for example, chemically, through heat, or via electromagnetic radiation (e.g., ultraviolet radiation) to form a solid polymer shell.

In one aspect of the invention, multiple emulsions can be formed that include amphiphilic species such as amphiphilic polymers and lipids and amphiphilic species typically includes a relatively hydrophilic portion, and a relatively hydrophobic portion. For instance, the hydrophilic portion may be a portion of the molecule that is charged, and the hydrophobic portion of the molecule may be a portion of the molecule that comprises hydrocarbon chains. The polymerosomes may be formed, for example, in devices such as those described above with respect to multiple emulsions. As mentioned above, one or more of the fluids forming the multiple emulsions may include polymers, such as copolymers, which can be subsequently polymerized. An example of such a system is normal butyl acrylate and acrylic acid, which can be polymerized to form a copolymer of poly(normal-butyl acrylate)-poly(acrylic acid).

When lipids are used, the resulting emulsion droplets are typically referred to as vesicles or lipid vesicles. When an amphiphilic polymer, such as a diblock copolymer, is used, the resulting droplets can be referred to as polymerosomes. "Polymers," as used herein, may include polymeric compounds, as well as compounds and species that can form polymeric compounds, such as prepolymers. Prepolymers include, for example, monomers and oligomers. In some cases, however, only polymeric compounds are used and prepolymers may not be appropriate.

Upon formation of a multiple emulsion, an amphiphilic species that is contained, dissolved, or suspended in the emulsion can spontaneously associate along a hydrophilic/hydrophobic interface in some cases. For instance, the hydrophilic portion of an amphiphilic species may extend into the aqueous phase and the hydrophobic portion may extend into the non-aqueous phase. Thus, the amphiphilic species can spontaneously organize under certain conditions so that the amphiphilic species molecules orient substantially parallel to each other and are oriented substantially perpendicular to the interface between two adjoining fluids, such as an inner droplet and outer droplet, or an outer droplet and an outer fluid. As the amphiphilic species become organized, they may form a sheet, e.g., a substantially spherical sheet, with a hydrophobic surface and an opposed hydrophilic surface. Depending on the arrangement of fluids, the hydrophobic side may face inwardly or outwardly and the hydrophilic side may face inwardly or outwardly. The resulting multiple emulsion structure may be a bilayer or a multi-lamellar structure.

In one set of embodiments, a method of forming multiple emulsion structures containing amphiphilic species, such as polymer vesicles or "polymerosomes," involves the removal of a portion of the middle fluid after the formation of a multiple emulsion. For instance, a component of the middle fluid, such as a solvent or carrier, can be removed from the fluid, in part or in whole, through evaporation or diffusion. The remaining component or components of the middle fluid may self-organize or otherwise harden as a result of the reduction in the amount of solvent or carrier in the middle fluid, similar to those processes previously described. This shell formation can occur, for example, through crystallization or self-assembly of polymers dissolved in the middle fluid. For instance, a surfactant or surfactants can be used so that when the surfactant concentration in the middle fluid increases (e.g., concurrently with a decrease in the solvent concentration) the surfactant molecules are oriented so that like regions of the surfactant are associated with the inner droplet and/or the outer fluid. Within the shell itself (i.e., the middle fluid), different regions of the surfactant molecules may associate with each other, resulting in a concentrating of materials that then form a membrane of lamellar sheet(s) composed primarily or substantially of surfactant. The membrane may be solid or semi-solid in some cases. Non-surfactants can also be used.

In some cases, the middle fluid comprises a solvent system used as a carrier, and a dissolved or suspended polymer such as a diblock copolymer, which can be amphiphilic. After formation of a multiple emulsion, the solvent can be removed from the shell using techniques such as evaporation or diffusion, leaving the diblock copolymers behind. As the solvent leaves the middle fluid layer, the polymers can self-assemble into single or multiple layers on the inner and/or outer surfaces, resulting in a polymerosome. This can result in a thin membrane that is capable of carrying, protecting, and delivering the inner droplet. Once formed, these polymerosomes can be removed from the outer fluid, dried, stored, etc.

In cases where it may be desirable to remove a portion of the middle fluid from the outer drop, for example, when forming a shell through self-assembly, some of the components of the middle fluid may be at least partially miscible in the outer fluid. This can allow the components to diffuse over time into the outer solvent, reducing the concentration of the components in the outer droplet, which can effectively increase the concentration of any of the immiscible components, e.g., polymers or surfactants, that comprise the outer droplet. This can lead to the self-assembly or gelation of polymers or other shell precursors in some embodiments, and can result in the formation of a solid or semi-solid shell. During droplet formation, it may still be preferred that the middle fluid be at least substantially immiscible with the outer fluid. This immiscibility can be provided, for example, by polymers, surfactants, solvents, or other components that form a portion of the middle fluid, but are not able to readily diffuse, at least entirely, into the outer fluid after droplet formation. Thus, the middle fluid can include, in certain embodiments, both a miscible component that can diffuse into the outer fluid after droplet formation, and an immiscible component that helps to promote droplet formation.

Other amphiphilic species may also be used, besides diblock copolymers. For example, other polymers, or other species such as lipids or phospholipids may be used with the present invention. For example, liposomes can also be formed from phospholipids and/or other lipids. For example, lipids or phospholipids may be provided instead of polymers in the methods described above. Other methods may also be used to produce robust encapsulants, for example, surface-induced polymerization of either the inner or outer interface, or temperature-induced gelation of the inner or middle fluid.

In one embodiment, an asymmetric liposome is provided, i.e., a liposome comprising a lipid bilayer having a first, inner surface comprising a first lipid composition and a second outer surface comprising a second lipid composition distinguishable from the first lipid composition, where the first, inner surface and the second, outer surface together form a lipid bilayer membrane defining the liposome, or at least one shell of the liposome if the liposome is a multilamellar liposome. Such a liposome may be formed, for example, by incorporating a first lipid in a first droplet and a second lipid in a second droplet surrounding the first droplet in a multiple emulsion, then removing the solvent can be removed from the shell using techniques such as evaporation or diffusion, leaving the lipids behind. As mentioned, higher degrees of nesting, i.e., to produce multilamellar liposomes, can also be fabricated, e.g., a first shell of a liposome may comprise a first, inner surface comprising a first lipid composition and a second outer surface comprising a second lipid composition distinguishable from the first lipid composition, and a second shell comprising a first, inner surface comprising a third lipid composition and a second outer surface comprising a fourth lipid composition distinguishable from the third lipid composition.

Figure 19:
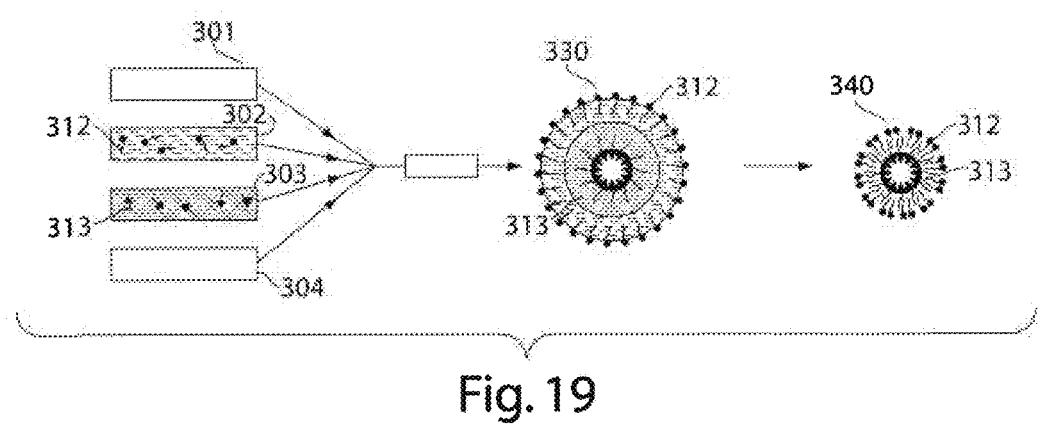
FIG. 19 is a schematic illustrating the formation of asymmetric liposomes, according to still another embodiment of the invention.

An example of such a process used to make an asymmetric liposome is shown in FIG. 19. In this figure, an inner fluid 301, a first middle fluid 302 (containing first lipids 312), a second middle fluid 303 (containing second lipids 313), and an outer fluid 304 are combined within microfluidic device 320, such as the ones described herein, e.g., in FIG. 17, to produce triple emulsion 330. As shown in FIG. 19, first middle fluid 302, containing lipids 312, may be present at one location within the triple emulsion, while second middle fluid 303, containing lipids 313, may be present within a different location without the triple emulsion, for example, lipids 312 may be arranged on the periphery of the triple emulsion, while lipids 313 are attracted to the center interface of the triple emulsion 330 (between the second middle fluid and the inner fluid). Subsequently, upon evaporation or one or more of the middle fluids, an asymmetric vesicle 340, such as an asymmetric liposome, may be formed, in which lipids 312 form an outer portion of a lipid bilayer membrane, while lipids 313 form an inner portion of the lipid bilayer membrane that defines the asymmetric liposome.

In another embodiment, a colloidosome is produced, i.e., a fluidic droplet surrounded by a shell of colloidal particles. Such a colloidosome can be produced, for example, by providing colloidal particles in a shell of a multiple emulsion droplet (e.g., in an outer droplet), then removing the solvent can be removed from the shell using techniques such as evaporation or diffusion, leaving the colloids behind to form the colloidosome. Nested colloidosomes can also be produced in some cases, i.e., a colloidosome having at least a first particle shell and a second particle shell surrounding the first particle shell. The shells may or may not have the same composition of colloids. Such a nested colloidosome can be produced, according to one set of embodiments, by producing a multiple emulsion having an inner droplet, a middle droplet, and an outer droplet (etc., if higher degrees of nesting are desired), where some or all of the middle droplet(s) and outer droplets contain colloidal particles. Next, the solvents can be removed from the shells using techniques such as evaporation or diffusion, leaving behind multiple layers of colloids to from the nested colloidosome.

In still other embodiments, any combination of the above-described systems may also be used. For example, in one embodiment, a particle may be produced comprising a lipid bilayer and a colloidal layer (in any order), a lipid bilayer and a polymer layer, a colloidal layer and a polymer layer, etc.

In another set of embodiments, fluid can be removed from an inner droplet in order to, for example, concentrate any species that may be contained within the inner droplet. Fluid may be removed from the inner droplet, or the inner droplet may be concentrated, using techniques similar to those described herein for removing fluid from an outer droplet. For instance, fluid can diffuse from or evaporate out of the inner droplet in order to reduce the size of the inner droplet, and therefore concentrate any components of the inner droplet that do not substantially diffuse or evaporate. For example, the volume of an inner droplet can be reduced by more than 50%, 75%, 90%, 95%, 99%, or 99.9%. Thus, the core radius of the inner droplet can be reduced by, for example, a factor of 2, 5, 10, or more, in some cases.

Fluid components can be chosen by those skilled in the art for particular diffusion or evaporative characteristics. The middle fluid (outer droplet) can also be selected so that the middle fluid provides for transfer of the inner fluid, either into or through the middle fluid. The size (thickness) of the outer droplet may also affect the rate of transfer out of the inner droplet, and in some cases the thickness of the outer droplet can be selected in order to control the rate at which inner fluid is removed from the inner droplet. Those of ordinary skill in the art will be able to optimize such a system, using no more than routine skill, to achieve a desired diffusion or evaporate a characteristic, depending on the particular application.

In another aspect, the methods and apparatus of the invention can be used to form droplets containing species and to provide methods of delivering such species. The species may be any substance that can be contained in any portion of the droplet and can be differentiated from the droplet fluid. The species may be present in any fluidic within droplet, for example, within an inner droplet and/or within an outer droplet, etc. Species may include, for example, pharmaceutical agents, drugs, DNA, RNA, proteins, fragrance, reactive agents, biocides, fungicides, preservatives, chemicals, or cells. Cells, for example, can be suspended in a fluid multiple emulsion, or contained in a polymerosome. One or more cells and one or more cell types can be contained in a droplet. The inner fluid may be, for example, an aqueous buffer solution. As the polydispersity and size of the droplets can be narrowly controlled, emulsions can be formed that include a specific number of species or particles per droplet. For instance, a single droplet may contain 1, 2, 3, 4, or more species. Emulsions can be formed with low polydispersity so that greater than 90%, 95%, or 99% of the droplets formed contain the same number of species. For example, an emulsion can be formed in which greater than about 95% of the droplets formed contain a single cell at the point of droplet production, without a need to separate or otherwise purify the emulsion in order to obtain this level of dispersity. Typically, the fluid supporting the cell is the inner fluid and is aqueous based. The middle fluid may be a non-aqueous fluid and the outer fluid may be an aqueous fluid. If a polymerosome is used, the shell may be formed of a material capable of protecting the cell. The shell may help retain, for example, moisture, and can be sized appropriately to maximize the lifetime of the cell within the polymerosome. For instance, the shell (outer droplet) may be sized to contain a specific volume, e.g., 10 nL, of inner fluid as well as a single cell or a select number of cells. Likewise, cells may be suspended in the bulk inner fluid so that, statistically, one cell will be included with each aliquot (e.g., 10 nL) of inner fluid when the inner fluid is used to form a droplet.

According to still another set of embodiments, a specific shell material may be chosen to dissolve, rupture, or otherwise release its contents under certain conditions. For example, if a polymerosome contains a drug, the shell components may be chosen to dissolve under certain physiological conditions (e.g., pH, temperature, osmotic strength), allowing the drug to be selectively released. Materials useful in these "smart capsules" are known to those skilled in the art. If it is desired that the inner species be dried, the shell material may be of a substance that is permeable to water molecules.

A variety of materials and methods, according to certain aspects of the invention, can be used to form any of the above-described components of the systems and devices of the invention. In some cases, the various materials selected lend themselves to various methods. For example, various components of the invention can be formed from solid materials, in which the channels can be formed via micromachining, film deposition processes such as spin coating and chemical vapor deposition, laser fabrication, photolithographic techniques, etching methods including wet chemical or plasma processes, and the like. See, for example, *Scientific American*, 248:44-55, 1983 (Angell, et al). In one embodiment, at least a portion of the fluidic system is formed of silicon by etching features in a silicon chip. Technologies for precise and efficient fabrication of various fluidic systems and devices of the invention from silicon are known. In another embodiment, various components of the systems and devices of the invention can be formed of a polymer, for example, an elastomeric polymer such as polydimethylsiloxane ("PDMS"), polytetrafluoroethylene ("PTFE" or Teflon®), or the like.

Different components can be fabricated of different materials. For example, a base portion including a bottom wall and side walls can be fabricated from an opaque material such as silicon or PDMS, and a top portion can be fabricated from a transparent or at least partially transparent material, such as glass or a transparent polymer, for observation and/or control of the fluidic process. Components can be coated so as to expose a desired chemical functionality to fluids that contact interior channel walls, where the base supporting material does not have a precise, desired functionality. For example, components can be fabricated as illustrated, with interior channel walls coated with another material. Material used to fabricate various components of the systems and devices of the invention, e.g., materials used to coat interior walls of fluid channels, may desirably be selected from among those materials that will not adversely affect or be affected by fluid flowing through the fluidic system, e.g., material(s) that is chemically inert in the presence of fluids to be used within the device.

In one embodiment, various components of the invention are fabricated from polymeric and/or flexible and/or elastomeric materials, and can be conveniently formed of a hardenable fluid, facilitating fabrication via molding (e.g. replica molding, injection molding, cast molding, etc.). The hardenable fluid can be essentially any fluid that can be induced to solidify, or that spontaneously solidifies, into a solid capable of containing and/or transporting fluids contemplated for use in and with the fluidic network. In one embodiment, the hardenable fluid comprises a polymeric liquid or a liquid polymeric precursor (i.e. a "prepolymer"). Suitable polymeric liquids can include, for example, thermoplastic polymers, thermoset polymers, or mixture of such polymers heated above their melting point. As another example, a suitable polymeric liquid may include a solution of one or more polymers in a suitable solvent, which solution forms a solid polymeric material upon removal of the solvent, for example, by evaporation. Such polymeric materials, which can be solidified from, for example, a melt state or by solvent evaporation, are well known to those of ordinary skill in the art. A variety of polymeric materials, many of which are elastomeric, are suitable, and are also suitable for forming molds or mold masters, for embodiments where one or both of the mold masters is composed of an elastomeric material. A non-limiting list of examples of such polymers includes polymers of the general classes of silicone polymers, epoxy polymers, and acrylate polymers. Epoxy polymers are characterized by the presence of a three-membered cyclic ether group commonly referred to as an epoxy group, 1,2-epoxide, or oxirane. For example, diglycidyl ethers of bisphenol A can be used, in addition to compounds based on aromatic amine, triazine, and cycloaliphatic backbones. Another example includes the well-known Novolac polymers. Non-limiting examples of silicone elastomers suitable for use according to the invention include those formed from precursors including the chlorosilanes such as methylchlorosilanes, ethylchlorosilanes, phenylchlorosilanes, etc.

Silicone polymers are preferred in one set of embodiments, for example, the silicone elastomer polydimethylsiloxane. Non-limiting examples of PDMS polymers include those sold under the trademark Sylgard by Dow Chemical Co., Midland, Mich., and particularly Sylgard 182, Sylgard 184, and Sylgard 186. Silicone polymers including PDMS have several beneficial properties simplifying fabrication of the microfluidic structures of the invention. For instance, such materials are inexpensive, readily available, and can be solidified from a prepolymeric liquid via curing with heat. For example, PDMSs are typically curable by exposure of the prepolymeric liquid to temperatures of about, for example, about 65° C. to about 75° C. for exposure times of, for example, about an hour. Also, silicone polymers, such as PDMS, can be elastomeric, and thus may be useful for forming very small features with relatively high aspect ratios, necessary in certain embodiments of the invention. Flexible (e.g., elastomeric) molds or masters can be advantageous in this regard.

One advantage of forming structures such as microfluidic structures of the invention from silicone polymers, such as PDMS, is the ability of such polymers to be oxidized, for example by exposure to an oxygen-containing plasma such as an air plasma, so that the oxidized structures contain, at their surface, chemical groups capable of cross-linking to other oxidized silicone polymer surfaces or to the oxidized surfaces of a variety of other polymeric and non-polymeric materials. Thus, components can be fabricated and then oxidized and essentially irreversibly sealed to other silicone polymer surfaces, or to the surfaces of other substrates reactive with the oxidized silicone polymer surfaces, without the need for separate adhesives or other sealing means. In most cases, sealing can be completed simply by contacting an oxidized silicone surface to another surface without the need to apply auxiliary pressure to form the seal. That is, the pre-oxidized silicone surface acts as a contact adhesive against suitable mating surfaces. Specifically, in addition to being irreversibly sealable to itself, oxidized silicone such as oxidized PDMS can also be sealed irreversibly to a range of oxidized materials other than itself including, for example, glass, silicon, silicon oxide, quartz, silicon nitride, polyethylene, polystyrene, glassy carbon, and epoxy polymers, which have been oxidized in a similar fashion to the PDMS surface (for example, via exposure to an oxygen-containing plasma). Oxidation and sealing methods useful in the context of the present invention, as well as overall molding techniques, are described in the art, for example, in an article entitled "Rapid Prototyping of Microfluidic Systems and Polydimethylsiloxane," *Anal. Chem.*, 70:474-480, 1998 (Duffy, et al.), incorporated herein by reference.

In some embodiments, certain microfluidic structures of the invention (or interior, fluid-contacting surfaces) may be formed from certain oxidized silicone polymers. Such surfaces may be more hydrophilic than the surface of an elastomeric polymer. Such hydrophilic channel surfaces can thus be more easily filled and wetted with aqueous solutions.

In one embodiment, a bottom wall of a microfluidic device of the invention is formed of a material different from one or more side walls or a top wall, or other components. For example, the interior surface of a bottom wall can comprise the surface of a silicon wafer or microchip, or other substrate. Other components can, as described above, be sealed to such alternative substrates. Where it is desired to seal a component comprising a silicone polymer (e.g. PDMS) to a substrate (bottom wall) of different material, the substrate may be selected from the group of materials to which oxidized silicone polymer is able to irreversibly seal (e.g., glass, silicon, silicon oxide, quartz, silicon nitride, polyethylene, polystyrene, epoxy polymers, and glassy carbon surfaces which have been oxidized). Alternatively, other sealing techniques can be used, as would be apparent to those of ordinary skill in the art, including, but not limited to, the use of separate adhesives, thermal bonding, solvent bonding, ultrasonic welding, etc.

The following applications are each incorporated herein by reference: U.S. Provisional Patent Application Ser. No. 60/659,045, filed Mar. 4, 2005, by Weitz, et al.; U.S. Provisional Patent Application Ser. No. 60/498,091, filed Aug. 27, 2003, by Link, et al.; U.S. Provisional Patent Application Ser. No. 60/392,195, filed Jun. 28, 2002, by Stone, et al.; U.S. Provisional Patent Application Ser. No. 60/424,042, filed Nov. 5, 2002, by Link, et al.; U.S. Pat. No. 5,512,131, issued Apr. 30, 1996 to Kumar, et al.; International Patent Publication WO 96/29629, published Jun. 26, 1996 by Whitesides, et al.; U.S. Pat. No. 6,355,198, issued Mar. 12, 2002 to Kim, et al.; International Patent Application Serial No.: PCT/US01/16973, filed May 25, 2001 by Anderson, et al., published as WO 01/89787 on Nov. 29, 2001; International Patent Application Serial No. PCT/US03/20542, filed Jun. 30, 2003 by Stone, et al., published as WO 2004/002627 on Jan. 8, 2004; International Patent Application Serial No. PCT/US2004/010903, filed Apr. 9, 2004 by Link, et al.; U.S. Provisional Patent Application Ser. No. 60/461,954, filed Apr. 10, 2003, by Link, et al.; International Patent Application Serial No. PCT/US2004/027912, filed Aug. 27, 2004, by Link, et al.; U.S. Provisional Patent Application Ser. No. 60/659,046, filed Mar. 4, 2005, entitled "Systems and Methods of Forming Particles," by Garstecki, et al.; and a U.S. utility patent application, entitled "Systems and Methods of Forming Particles," by Garstecki, et al., filed on even date herewith.

The following examples are intended to illustrate certain embodiments of the present invention, but do not exemplify the full scope of the invention.

EXAMPLE 1

Figure 5A:
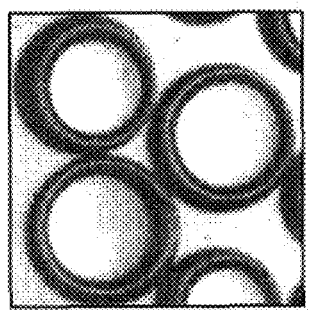
FIGS. 5A-5F are copies of photomicrographs showing various hardened-shell polymerosomes in still other embodiments of the invention.
Figure 5B:
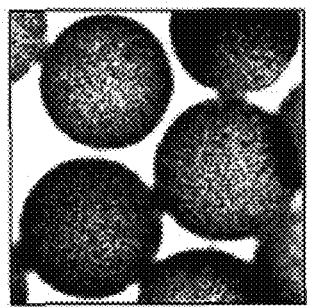
Figure 5C:
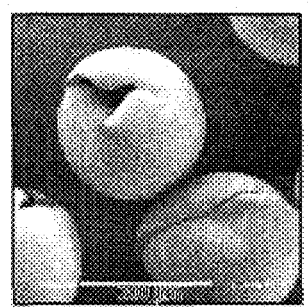

To demonstrate capsule production, a rigid spherical shell was fabricated by photopolymerizing a polymer (Norland Optical Adhesive, NJ) contained in the middle fluid. The adhesive was diluted with acetone by 30% to decrease its viscosity. After generating the multiple emulsions using the acetone/adhesive solution as a middle fluid, the shell was formed by polymerizing the resulting droplets with an ultraviolet light source for approximately 10 seconds as the multiple emulsion droplets traversed the collection tube. Bright field images of the multiple emulsions and the resulting solid shells are shown in FIGS. 5A and 5B, respectively. To confirm that the outer droplet (middle fluid) had formed a solid shell, the spheres were crushed between two microscope cover slides. The cracked polymer shells are evident in the scanning electron micrograph image shown in FIG. 5C.

EXAMPLE 2

In another technique for forming polymerosomes, multiple emulsions were created with a single internal drop, and diblock copolymers were dissolved in the intermediate, or middle, fluid. A volatile fluid was used as a component of the intermediate phase, and was subsequently evaporated, allowing the diblock copolymers to organize into lamellar and/or multi-lamellar shells, thus forming polymerosomes. As the multiple emulsion droplet morphology can be carefully controlled, controllable polymerosomes can be made, as was illustrated. For instance, polymerosomes may be made consistently monodisperse, e.g., of consistent size, and/or of consistent shell thickness. This consistency can be achieved by forming the multiple emulsion in a single step and then by subsequently hardening the shell, as shown in this example.

Figure 5D:
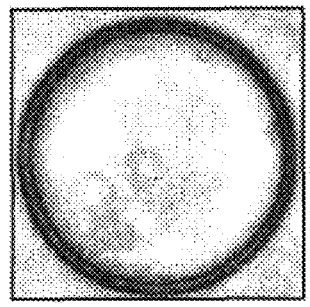
Figure 5E:
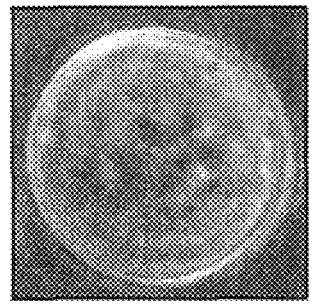
Figure 5F:
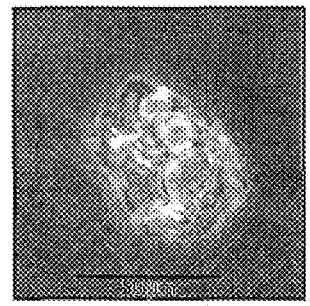

To illustrate this level of control, a water-in-oil-in-water multiple emulsion with a middle fluid composed of 70% toluene and 30% tetrahydrofuran (THF) was generated. The components of this middle fluid served as a carrier fluid for a diblock copolymer, poly(butyl acrylate)-b-poly(acrylic acid) (FIG. 5D). As the solvent evaporated after formation of the multiple emulsion, the amphiphilic polymers self-assembled into layers on both interfaces, forming a polymerosome. The polymer layer can be made extremely thin, making it difficult to resolve in bright field microscopy; a phase contrast image of a typical polymer vesicle is shown in FIG. 5E. To confirm that these structures were indeed polymerosomes, they were "deflated" with osmotic stress through addition of a sucrose solution (0.1 M) to the continuous fluid. The polymerosome from FIG. 5E, deflated in this way, is shown in FIG. 5F. During the procedure, the inner and outer fluids remained separate, providing for efficient and robust encapsulation. Thus, any contact or contamination between the inner and outer fluids can be avoided, even when the two fluids are partially or totally miscible.

In cases where it may be desirable to remove a portion of the middle fluid from the outer droplet, some of the components of the middle fluid may be at least partially miscible in the outer fluid. This can allow the components to diffuse over time into the outer solvent, reducing the concentration of the components in the outer droplet, effectively increasing the concentration of any immiscible components, e.g., polymers or surfactants, that comprise the outer droplet. This can lead to tighter organization of the polymeric components, and eventually the formation of a shell. During droplet formation, it may still be desirable that the middle fluid be substantially immiscible with the outer fluid. This immiscibility can be provided, for example, by polymers, surfactants, solvents, or other components that form a portion of the middle fluid that are not able to diffuse, at least entirely, into the outer fluid after droplet formation. Thus, the middle fluid can include, e.g., both a miscible component that can diffuse into the outer fluid after droplet formation, and an immiscible component that helps to promote droplet formation.

In addition to polymerosomes, liposomes can also be formed from phospholipids in a similar manner. Alternatively, other methods to produce robust encapsulants may include, for example, surface-induced polymerization of either or both the inner or outer interface, and/or temperature-induced gelation of the inner and/or middle fluid.

EXAMPLE 3

This example illustrates that the size distribution of multiple emulsions may be controlled by the break-up mechanism, according to one embodiment of the invention.

In a device having the geometry shown in FIG. 1, multiple emulsions may be generated. They may be generated when fluids passing through the device are in a dripping regime (FIG. 3A) or a jetting regime (FIG. 3B). The dripping and jetting mechanisms are closely related, and the transition between them can be controlled by controlling the flowrate of the fluids through the device, for example, by controlling the flowrate of the outer most fluid.

Figure 6A:
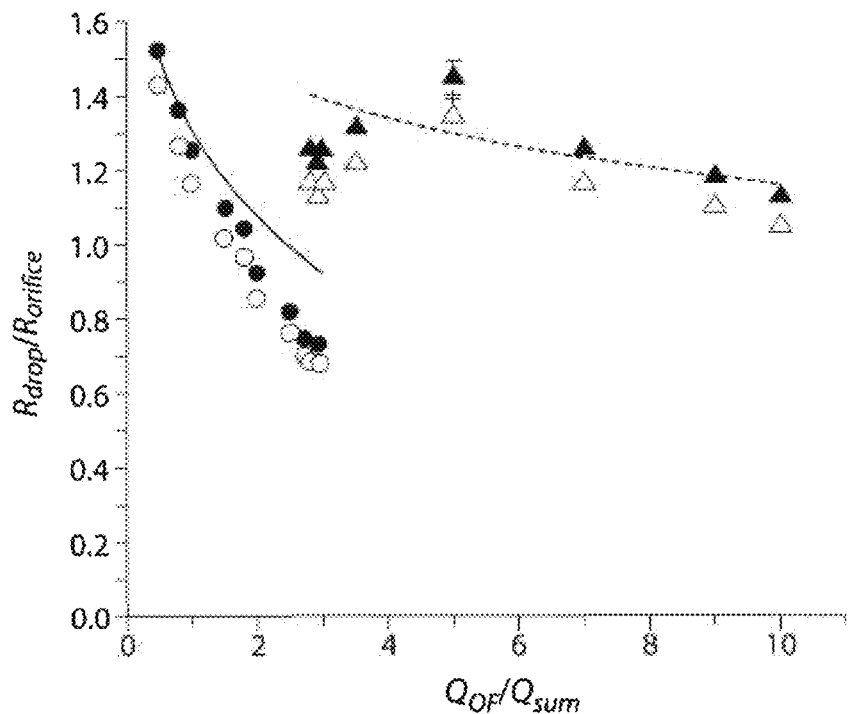
FIGS. 6A-6B graphically illustrate data showing the relationship between droplet size and flowrate, according to another embodiment of the invention.
Figure 6B:
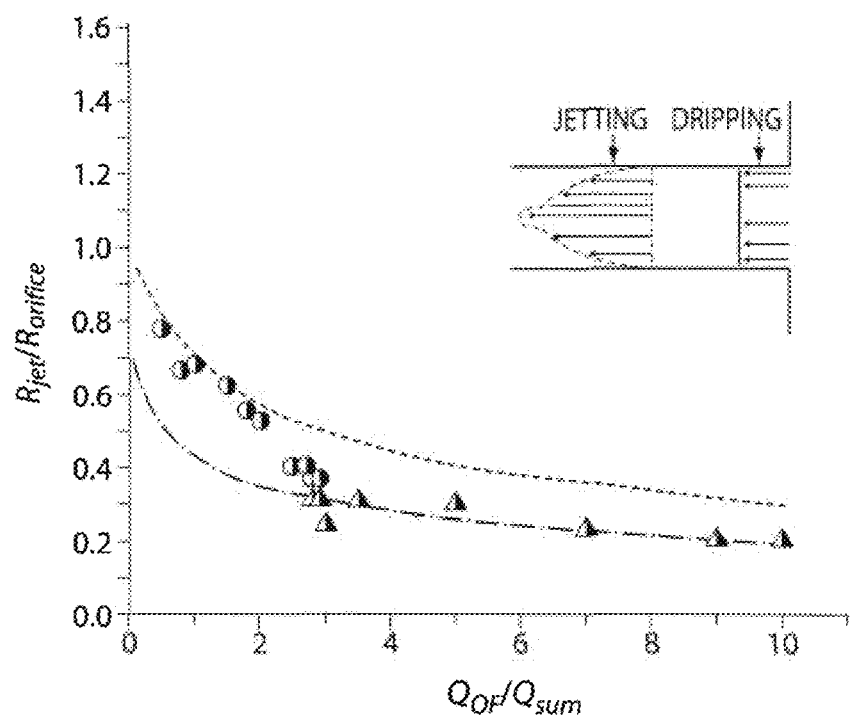
Figure 11A:
FIGS. 11A-11G illustrate the evolution of polymerosomes under osmotic pressure shock, in still another embodiment of the invention.
Figure 11B:
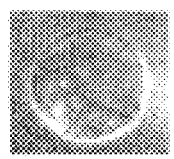
Figure 11C:
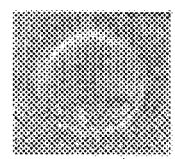
Figure 11D:
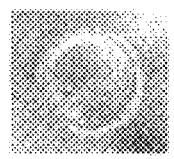
Figure 11E:
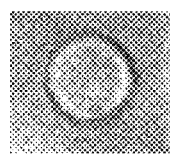
Figure 11F:
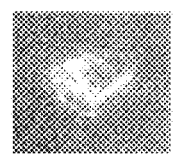
Figure 11G:
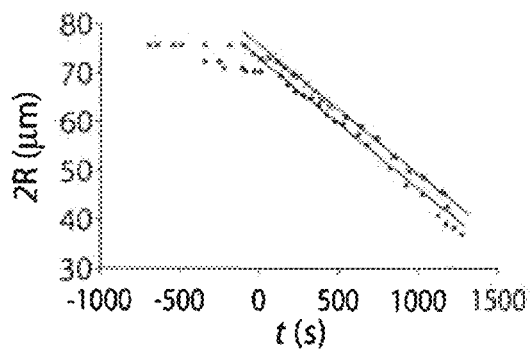
Figure 12A:
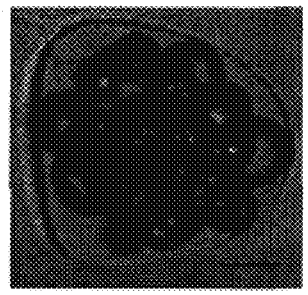
FIGS. 12A-12C illustrate certain double emulsions containing many internal droplets and multi-compartmental vesicular structure.
Figure 12B:
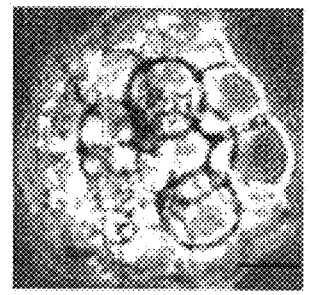
Figure 12C:
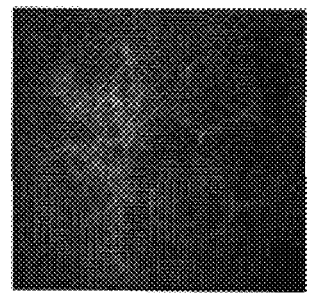

FIGS. 6A and 6B illustrate how a change in the outer flowrate, $Q_{OF}$ in relation to the total flow can affect the size of the outer emulsion droplets that are produced. The radius of the outer emulsion droplets, $R_{drop}$, decreases linearly with $Q_{OF}$, as shown by the circles in FIG. 6A. However, increasing $Q_{OF}$ beyond a threshold value caused the jet to abruptly lengthen, signifying the transition to the jetting regime. At this flowrate, a discontinuous increase in $R_{drop}$ occurred, as shown by the triangles in FIG. 6A. In contrast, the radius of the coaxial jet, $R_{jet}$, measured near the exit orifice, decreased monotonically through the transition, as shown in FIG. 6B. The droplet production frequency also decreased correspondingly.

Figure 4:
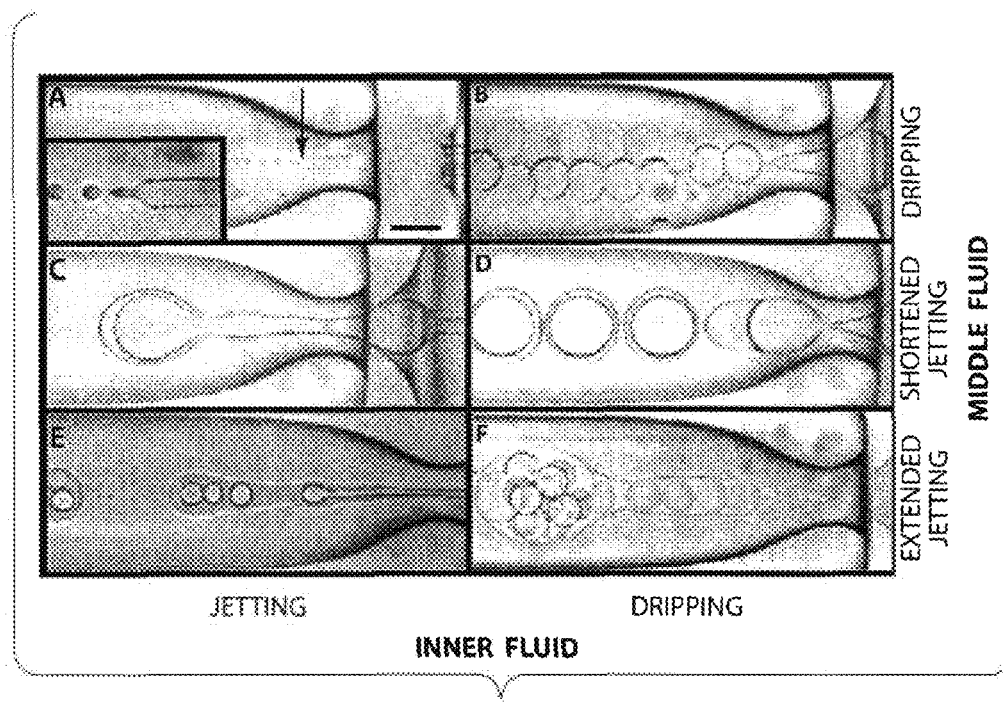
FIG. 4 illustrates various photomicrographs showing the formation of a variety of multiple emulsions in other embodiments of the invention.

FIG. 3 is a photomicrograph showing steady-state droplet formation mechanisms that can result in monodisperse multiple emulsions with a single internal droplet: (A) dripping and (B) jetting. In both cases, the rate of droplet formation was the same for the inner and middle fluids, meaning that each inner droplet was contained in a single outer droplet. The transition between dripping and jetting was controlled by the flowrate of outer fluid 160, $Q_{OF}$, for fixed total flow rates of the inner and middle fluids. The multiple emulsions in (A) exhibited a polydispersity of less than about 1%, while those in (B) had a polydispersity of about 3%. The inset in FIG. 3B shows the "pinch-off" of the multiple emulsion droplets from the coaxial jet. The same device and same fluids were used for the experiments described in FIGS. 3, 4, and 6. The outer fluid used was silicon oil with a viscosity $\eta_{OF}$=0.48 Pa·s, the middle fluid was a glycerol-water mixture with a viscosity $\eta_{MF}$=0.05 Pa·s and the inner fluid was silicon oil with a viscosity $\eta_{IF}$=0.05 Pa·s. Interfacial tension for the aqueous mixture and silicon oil without surfactants was approximately 20 mN/m. The flow rates of the fluids in (A) were $Q_{OF}$=2500 microliter hr$^{-1}$, $Q_{MF}$=200 microliter hr$^{-1}$, and $Q_{IF}$=800 microliter hr$^{-1}$. The flow rates in (B) were $Q_{OF}$=7000 microliter hr$^{-1}$, $Q_{MF}$=200 microliter hr$^{-1}$, and $Q_{IF}$=800 microliter hr$^{-1}$.

The following analysis is presented to explain some of the observed results. However, it is to be understood that this mathematical analysis is not intended to be binding, but merely of a proposed description of an observed phenomenon. By matching the viscosities of the innermost and middle fluids, $\eta_{IF}=\eta_{MF}$, the velocity profile of the coaxial jet could be made equivalent to that of a single fluid with the same viscosity. The growth rate of a perturbation could be determined by its velocity perpendicular to the interface, $v_\perp \approx \gamma/\eta_{OF}$, where $\gamma$ is the interfacial tension, leading to a droplet pinch-off time of $t_{pinch}=CR_{jet}\eta_{OF}/\gamma$. numerical calculations gave $C \approx 20$ when $\eta_{IF}/\eta_{OF}=0.1$. While strictly valid for a cylinder of a single fluid; for a coaxial fluid thread, the effective surface tension may be modified by the fact that there are two interfaces. However, Rayleigh-Plateau instability cannot occur until the length of the jet has grown to be comparable to its radius; this takes a time $t_g \approx R_{jet}^3/Q_{sum}$, where $Q_{sum}$ is the net flowrate of the two inner fluids. If, for example, the pinch-off time is less than the growth time, droplets will be formed as soon as the jet is large enough to sustain the instability, which will occur just inside the outlet; this leads to the dripping regime as illustrated in FIG. 3A. By contrast, if $t_{pinch} > t_g$, the jet will grow faster that the droplets can form and will lead to the jetting regime, where the droplets are formed downstream, farther inside the outlet, as illustrated in FIG. 3B. An effective capillary number (Ca) of the interface can be defined by $$Ca = \frac{t_{pinch}}{t_g} = \frac{\eta_{OF} Q_{sum}}{\gamma R_{jet}^2} = \frac{\eta_{OF} v}{\gamma},$$

where v is the downstream velocity of the inner fluids; this governs the transition between dripping and jetting that occurs when $Ca \approx 1$. Expressing the control parameter in terms of a capillary number helps to capture the physically observed phenomenon picture that the transition from dripping to jetting occurs when viscous stresses on the interface due to the fluid flow become so large that the Rayleigh-Plateau instability is suppressed in these system geometries.

Using this physical picture, $R_{jet}$ and $R_{drop}$ could be determined as a function of $Q_{OF}$ by considering the velocity flow profiles in both the jetting and dripping regimes. However, these velocity profiles may evolve as the fluids enter and move downstream through the collection tube, and therefore a different treatment for each mechanism may prove useful.

When a coaxial jet first enters the exit orifice, the velocity profile of the fluids is approximately flat across the channel, as depicted in the right inset in FIG. 6B; it may remain this way for a distance comparable to the orifice radius times the Reynolds number. Thus, in the dripping regime, where droplets form very close to the orifice, mass flux can be related to cross-sectional area as follows:

$$\frac{Q_{sum}}{Q_{OF}} = \frac{\pi R_{jet}^2}{\pi R_{orifice}^2 - \pi R_{jet}^2},$$

where $R_{orifice}$ is the radius of the exit orifice. The values of $R_{jet}/R_{orifice}$ predicted from this equation, with no adjustable parameters, were in good agreement with the measured values in the dripping regime, as shown in FIG. 6B (dotted line). Comparison of the measured radii of the droplets and the coaxial jet showed that $R_{drop}=1.87\ R_{jet}$; this empirical relationship was consistent with theoretical calculations of the droplet size for the breakup of an infinitely long cylindrical thread in an ambient fluid for $\eta_{IF}/\eta_{OF}=0.1$. From this, $R_{drop}$ was predicted and was found to be in good agreement with the data, as represented by the solid line in FIG. 6A. It is believed that the small discrepancy near the transition is likely a result of the deviation from a flat velocity profile.

In the jetting regime, where droplets are formed well downstream and well within the entrance orifice of the inner conduit, the fluid flow has evolved into the classic parabolic velocity profile of laminar pipe flow. The viscosity difference between the fluids cause the inner coaxial jet to develop a different velocity profile from that of the outer fluid. The full profiles can be determined by solving the Navier-Stokes equations in the low Reynolds number limit. The jet expanded slightly due to the widening taper of the collection tube, modifying the flow profiles. Using this system, the jet radii was predicted using no adjustable parameters, and good agreement was obtained with values measured before the jet has expanded, as shown by the dashed-dotted line in FIG. 6B.

Droplet formation in the jetting regime may be generally irregular, leading to more polydisperse size distribution. However, in some cases, stable droplet formation can be achieved, occurring at a fixed location on the jet. It is believed that this level of control is a result, at least in part, of the geometry of the collection tube, and specifically the result of an increasing inner diameter downstream of a narrow orifice. As illustrated in FIGS. 1 and 3, the collection tube (inner conduit) may include an internal taper that starts generally small at the exit orifice and gradually expands downstream of the orifice. This decrease in diameter may be continuous or stepped, and may or may not include a corresponding decrease in the outer diameter of the conduit. This may lead to an expansion of the jet diameter as the fluid flows downstream through the area of increasing inner diameter, and a concomitant decrease in the velocity results. As soon as Ca decreases sufficiently to sustain the Rayleigh-Plateau instability, the jet rupture, fixing the location and resulting in substantially monodisperse droplets. Thus, the systems described herein can provide a mechanism for producing substantially monodisperse droplets, including multiple emulsions, in the jetting regime. In the jetting regime, the frequency of rupture decreases, producing droplets which can be substantially larger than the size of the jet, i.e., the droplets may have a diameter that is, for example, greater than 1×, 2×, or 3× the radius of the jet, as illustrated in FIG. 4A. It takes time to fill the volume of these larger droplets, and mass conservation of the dispersed phases and the characteristic time scale for droplet break-off can be used to obtain $Q_{sum}=4/3\pi R_{drop}^3/t_{pinch}$. Solving for the droplet radius gives $$R_{drop} = \left(\frac{15 Q_{sum}}{\pi} \frac{R_{jet} \eta_{OF}}{\gamma}\right)^{1/3}.$$

This prediction provides a good match with empirical results as shown by the dashed line in FIG. 4A.

EXAMPLE 4

The use of diblock copolymers to generate polymer vesicles is an attractive strategy to create new structures for encapsulation. These structures are called polymerosomes, and like more traditional vesicles formed from bilayers of phospholipids, they can encapsulate nano- to picoliter volumes of fluid. In addition, the low toxicity of certain diblock copolymers makes these structures promising for drug delivery applications. Depending on the length and chemical nature of the copolymers, the resultant polymerosome can be much more robust than liposomes of comparable sizes. The flexibility afforded by the use of diblock copolymers may significantly increase the control over the properties of polymerosomes; the character of each block of the diblocks can be tuned to fit the desired application. For example, the membrane thickness can be controlled by varying the degree of polymerization of the individual diblock molecules, whereas fluidity and permeability of the membrane can be adjusted by changing the glass transition temperature of the hydrophobic block. Similarly, control over the nature of the individual polymer blocks can lead to alternative mechanisms to trigger release.

Polymerosomes can be spontaneously formed by precipitating block copolymers by adding a poor solvent for one of the diblocks. Alternatively, they can be formed by rehydrating a dried film of the copolymers. Rehydrating a lamellar structure of diblocks can cause them to assemble into layers that pucker and fuse to form vesicles, among other ordered structures such as micelles or wormlike micelles; however, the resultant polymerosomes may be polydisperse.

Encapsulation and film rehydration can be combined into one step by rehydrating the dried films with an aqueous solution that contains the desired material to be encapsulated; as the polymerosomes form, they trap some of the surrounding fluid within. Alternatively, the polymerosomes can be filled after they are formed by osmotically driving the desired materials inside. In these cases, however, the encapsulation efficiency is generally low. Furthermore, both encapsulation techniques present difficulties when encapsulating hydrophobic materials or materials that cannot be driven through the membrane. Thus, efficient use of polymerosomes in different encapsulation technologies requires new fabrication methodologies.

This example describes a new method to create highly uniform polymerosomes using a one-step process where the inner and outer fluids are maintained as completely separate streams; this ensures highly efficient encapsulation. A microfluidic technique is used to generate uniform double emulsions of water droplets surrounded by a layer of organic solvent; these droplet-in-droplet or core-shell structures may be dispersed in a continuous water phase. The diblock copolymers are dissolved in the organic solvent; these self-assemble on the concentric interfaces of the double emulsions. Polymerosomes are then formed by completely evaporating the organic solvent from the shell. This technique allows control of the size of the polymerosome and maintains separation of the internal fluids from the external fluid throughout the entire process, providing for highly efficient encapsulation.

To form the double emulsions, a microfluidic device was used having two round glass capillary tubes nested within an outer square tube; these round tubes are tapered at the ends, as shown in FIG. 7. The inner dimension of the outer square tube was equal to the outer dimension of the inner round tubes in this example; this simplified the alignment. The outer diameter of the round tubes was 1 mm, whereas the radii of the tapered orifices was between 20 and 100 micrometer. Three different fluids were simultaneously pumped into the system at controlled flow rates. The innermost fluid was pumped through the inner tube, whereas the middle fluid was pumped through the outer square capillary in the same direction (FIG. 7A). This produced a coaxial flow at the exit of the first tapered capillary tube. The outermost fluid was pumped from the opposite direction through the outer square capillary; it acted to hydrodynamically focus the middle and inner fluids through the second round capillary tube, as shown in FIG. 7A. FIG. 7A is a side view and FIG. 7B is a front view of the device. The three different fluids within the device are denoted as f1, f2, and f3, and were pumped into the device and forced to flow through the constriction with a radius a. The coaxial flow of the inner fluids was maintained through the second orifice where surface tension caused the fluid stream to break into droplets; surprisingly, the coaxial geometry was maintained and double emulsions were formed with no leakage of the inner fluid to the outer fluid.

The position of droplet formation depended on the flowrate of the outermost fluid. At low outer flow rates, double emulsion droplets were formed within about one orifice diameter of the entrance; by contrast, at higher flow rates, the neck was stretched into a coaxial thread that broke further downstream. The formation of droplets relatively close is referred to as orifice dripping, whereas the formation of droplets at the end of a relatively long thread is referred to as jetting. The droplets formed through the dripping mechanism were relatively monodisperse, whereas droplets formed through the jetting mechanism had a somewhat larger polydispersity.

Typically, the droplets formed through the dripping mechanism had very low polydispersities, less than about 3%, as observed in FIG. 8A. The number of small aqueous droplets contained within the larger oil droplets depended on the relative frequency of droplet formation for the innermost and middle fluids. If the innermost fluid broke into droplets more rapidly than the middle fluid, then large oil droplets were obtained that contained many small aqueous droplets. However, if the rate of droplet formation was about the same, double emulsions with a single inner droplet were formed.

This technique maintained complete separation of the internal and external fluids, making it useful for generating capsule geometries such as polymerosomes. The overall frequency of droplet production in the dripping regime could range from about 100 Hz to about 7000 Hz, which allowed the formation of up to about $10^7$ double emulsion droplets per hour.

To generate polymerosomes, a strategy that exploited the core-shell structures of the double emulsion was used. Water-in-oil-in-water double emulsions were generated with a diblock copolymer dissolved in an intermediate hydrophobic fluid. The inner aqueous phase was distilled water (Millipore), and the outer phase was a mixture of 80% (v/v) glycerol in distilled water. Glycerol was added to the outer fluid to increase its viscosity, which improved the efficiency of the flow focusing. The intermediate phase was a volatile organic solvent; the evaporation of the organic solvent caused the amphiphilic block copolymers to self-assemble, forming the polymerosome. In these experiments, the diblock copolymers poly(normal-butyl acrylate)-poly (acrylic acid) (PBA-PAA) were used. The PBA was the relatively hydrophobic block and had a molecular weight (MW) of about 4,000, whereas the PAA was the relatively hydrophilic block and had a MW of about 1,500. The dissolved diblocks in this example were mostly unimers (as opposed to larger aggregates), because the aggregates did not appear to efficiently stabilize the inner droplet against coalescence with the outer phase, and thus double emulsion break-up could occur.

Tetrahydrofuran (THF) was used as a solvent for both the PBA and the PAA blocks, since the diblocks dissolve as unimers in it; however, since THF was highly miscible with water, it could not be used alone as the organic solvent because the droplet formation required an interfacial tension between the middle fluid and the two others fluids. Therefore, a cosolvent mixture of THF and toluene was used. This mixture was still a good solvent for the diblock, while simultaneously having sufficiently large surface tension to enable droplet formation. Cosolvent mixtures of toluene and THF were used that varied from 50-50 wt %, respectively, to 80-20 wt %, and had between 0.1 wt % and 5 wt % PBA-PAA. Despite the addition of the large amount of toluene, which decreased the polar character of the organic mixture, the diblocks retained their amphiphilic nature and stabilized the double emulsion, as shown in FIG. 8A. This figure is a microscope image of the double emulsion formation in the capillaries, acquired with a high-speed video camera. In control experiments, it was confirmed that the stability imparted to the double emulsions by the diblocks could be important; without them, the inner water droplet did not maintain its integrity well and simply broke through the intermediate hydrophobic phase as shown in FIG. 8B. Thus, in FIG. 8A, 0.8 wt % of the copolymer was added to the cosolvent solution f2. In FIG. 8B, no diblocks were added to the cosolvent mixture, f2. Stable double emulsions were generated in FIG. 8A, whereas in FIG. 8B, the inner phase broke through the organic phase; only simple emulsions of the middle fluid in the continuous aqueous phase were observed. The radius of the constriction was 70 micrometers for both FIGS. 8A and 8B.

EXAMPLE 5

In this example, the formation of the PBA-PAA polymerosomes from double emulsions (prepared as in Example 4) was followed by monitoring the evaporation of the cosolvent mixture from the middle phase, as shown by the microscope images in FIG. 9. The two interfaces of the double emulsion separated by the thin shell of organic fluid can be observed (FIG. 9A), where the middle fluid layer was visible. As the organic solvents dissolved in the surrounding water and ultimately evaporated, the shell gradually became thinner and the interfaces tended to disappear; the bottom part appeared to vanish after the upper part, which may be due to inhomogeneity in the thickness of the organic fluid shell (FIGS. 9B and 9C). FIGS. 9A-9C are separated by 3 min. The scale bar in FIG. 9A represents 40 micrometers. Under bright field microscopy, the thin wall of the vesicle, which appeared to form after the solvents had evaporated, could not be readily observed because the refractive indices of the inner and outer fluids were nearly equal. However, phase contrast microscopy could be used to enhance the index-of-refraction mismatch between the membrane and the surrounding fluid, as shown in FIG. 9D. The scale bar in FIG. 9D represents 30 micrometers.

EXAMPLE 6

In this example, to characterize the nature of the membrane of the polymerosome, a small quantity of CdSe quantum dots were added to the inner fluid before the formation of the double emulsion; these served as fluorescent markers that could be trapped on the inner side of the walls of the polymerosome, providing a method of visualizing the membrane. A phase contrast image of a 70 micrometer vesicle is shown in FIG. 10A, and for comparison, a fluorescence image, with excitation at 488 nm, is shown in FIG. 10B; the ring of fluorescing quantum dots trapped in the wall of the membrane is readily observed.

The initial thickness of the shell was about 30 micrometers, and the initial diblock concentration was 0.5 wt %; since the radius of the shell remained the same, the final thickness would be about 1.5 micrometers if all of the solvent evaporated. This is consistent with the measured membrane thickness of a few microns; however, there is the possibility that a small amount of solvent remains, albeit only a small amount. The membrane does not appear to be unilamellar; the expected thickness of a bilayer of these diblocks is about 40 nm, suggesting that the shell is at least on the order of 100 layers thick in this case. However, the thickness of the wall could be controlled by adjusting the initial concentration of the diblock copolymers in the cosolvent mixture. No leakage of the fluorescent particles through the walls of the polymerosome was observed over at least several days, confirming that the self-assembled membrane was stable.

EXAMPLE 7

An interfacial tension between the middle fluid and both the inner and outer fluids may be important to drive the Rayleigh-Plateau instability that forms the double emulsions. However, a polymerosome should have a vanishing surface tension if the membrane is to be truly flexible. In this example, this is shown using poly(butyl acrylate), which has a glass transition temperature of −35° C., so the vesicle membrane is fluid. This can occur if substantially all of the solvent in the shell evaporates, leaving a membrane comprised of diblock copolymers.

To determine whether this occurs, the polymerosomes were subjected to an osmotic shock by introducing glucose to the outer, continuous phase, at a final concentration of approximately 100 mM, at a time taken as the origin. The final concentration of sucrose was approximately 100 mM. Before the addition of sucrose (t<0), the vesicle radius was generally constant. After the addition of sucrose (t>0), the resultant osmotic pressure "pumped" water out of the polymerosomes, and the vesicles shrank due to the osmotic pressure difference between the external and internal environments, as shown in the sequence of images in FIGS. 10A-10F. The interval between two successive images is 60 s, except for the last two images, which are separated by 5 min.

The deflation and collapse of the polymerosome appears to confirm that there was no remaining surface tension and that virtually all of the organic solvent had evaporated. However, liposomes and polymerosomes are known to undergo well-defined shape transformations as the osmotic pressure in the environment is varied; the collapsed morphology of the last image has never been reported. This may be an indication of the membrane heterogeneity or incomplete drying of the membrane.

The permeability of the membrane, P, was determined from the initial rate of change in the polymerosome radius, R, using the equation:

$$\frac{dR}{dt} = -\alpha P \Delta c,$$

where α (alpha) is the molar volume of water (alpha=18× $10^{-3}$ L/mol) and Δc (delta-c) (mol/L) is the difference in concentration of glucose between the inner and outer solutions. R appeared to decrease linearly in time, as shown in FIG. 10G for two different vesicles. In FIG. 10G, the radius of two polymerosomes of roughly the same initial radius are displayed as a function of time. The two polymerosomes were submitted to an osmotic pressure shock by placing them in a 100 mM glucose solution. The permeability of the polymerosomes was deduced from the slope of the linear regime that is observed for the two vesicles using the above equation, as follows. From the slope, it was determined that $P \approx 7 \pm 1$ micrometers/s, where the error reflects uncertainty in the glucose concentration. This value of permeability was comparable to that measured for others polymerosomes, $P \sim 10$ micrometers/s, and was about 10 times smaller than that measured for phospholipid vesicles, $P \sim 15$ to $150$ micrometers/s. In addition, these results suggested that the membrane thickness of the polymerosomes was probably not excessively large, as the permeability is comparable to that of others polymerosomes. Nevertheless, the membranes may still be somewhat heterogeneous; regions of non-uniform thickness can be observed in some polymerosomes. Moreover, some of the solvent may still remain trapped in the membrane, which may affect permeability.

EXAMPLE 8

The synthesis technique described in the above examples, of course, is not restricted to simple polymerosomes. Double emulsion droplets can also be formed that contain more than a single internal water droplet. These can be used to form a new class of polymerosome structures. This example illustrates such double emulsion droplets with many internal water droplets.

In FIG. 10A, the organic phase has been labeled with quantum dots to allow visualization by fluorescence microscopy. Surprisingly, the interior water droplets retained their integrity as the organic fluid evaporated. This resulted in the formation of a foamlike structure, with the final polymerosome having many internal compartments, as shown by the phase contrast image in FIG. 10B and the fluorescence image in FIG. 10C. The scale bars are 30 micrometers. These structures confirmed that the internal water droplets acted as a "template" for creating the polymerosome in the above-described synthesis techniques. Moreover, the flexibility afforded by this method allowed the creation of new classes of structures which may find additional uses as encapsulation structures.

EXAMPLE 9

Polymeric vesicles, or polymerosomes, are of interest for the encapsulation and delivery of active ingredients. They offer enhanced stability and lower permeability compared to lipid vesicles, and the versatility of synthetic polymer chemistry provides the ability to tune properties such as membrane thickness, surface functionality, and degradation kinetics. One approach to form large polymerosomes with diameters of 10 micrometers to 100 micrometers, illustrated in this example, is to use water-in-oil-in-water double emulsion droplets of controlled architecture as templates. A volatile organic solvent containing an amphiphilic diblock copolymer was used as the middle phase, as shown schematically in FIG. 13. This technique offers the advantages of high encapsulation efficiencies and controllable vesicle sizes and architectures.

Figure 13:
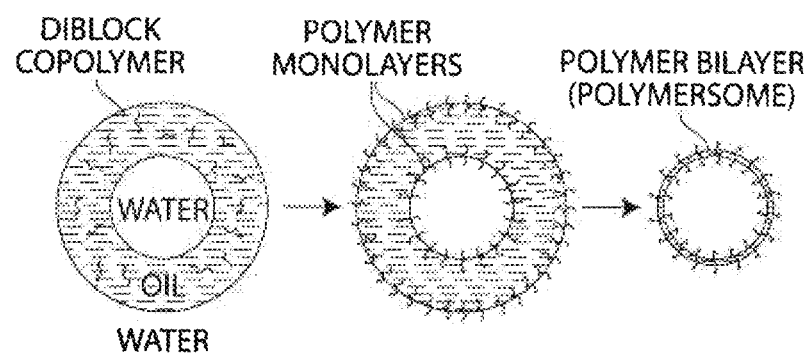
FIG. 13 is a schematic illustrating the formation of polymerosomes, according to yet another embodiment of the invention.

FIG. 13 is a schematic for the formation of polymerosomes from water-in-oil-in-water droplets. Initially, a double emulsion of single aqueous droplets within droplets of organic solvent was prepared using a microcapillary device. Amphiphilic diblock copolymers, dissolved in the middle phase, a volatile organic solvent, assembled into monolayers at the oil-water interfaces. Evaporation of the middle phase then lead to the formation of polymer bilayers (polymerosomes).

In this approach, the concentration of polymer in the organic phase is an important variable: if it is lower than the amount required to fully coat the oil-water interfaces, then the polymerosomes may not be stable. In practice, it is convenient to work with an excess concentration; indeed, this excess may be used to tune the thickness and structure of the polymerosome walls through formation of multi-layered copolymer interfaces.

Surprisingly, polymerosomes formed from double emulsions with poly(butyl acrylateblock-acrylic acid) (PBA-PAA) with relatively thick walls (about 1.5 micrometers) had permeabilities comparable to those of unilamellar polymersomes (about 10 nm to 20 nm thick). This suggested that there may be "defects" in the copolymer layer, which may be in the form of inhomogeneous thickness. To prepare uniform polymerosomes with well-controlled structures, it is generally important to understand how these thickness inhomogeneities may develop, and how their formation depends on polymer concentration.

In this example, the structural evolution during solvent evaporation from double emulsion droplets stabilized by a polystyrene-block-poly(ethylene oxide) (PS-PEO) diblock copolymer was investigated. It was found that, during evaporation, the majority of the organic phase dewets from a thin organic film separating the inner and outer aqueous phases, ultimately producing a polymerosome that was relatively thin over most of its surface. Dewetting implies the existence of an adhesive interaction between the aqueous phases that is comparable to the interfacial tension, as previously observed in both oil-in-water and water-in-oil single emulsion systems. This may arise from a depletion effect, due to excess diblock copolymer in the organic phase, and therefore that its strength may increase with polymer concentration. Thus, these results suggested that obtaining uniform polymerosomes using emulsion techniques requires control of the polymer concentration.

Double emulsion droplets of controlled architecture were produced using glass microcapillary devices, as previously described. The inner phase was 5 vol % glycerol in water, and the middle hydrophobic phase was 0.01 wt % to 1.5 wt % polymer in toluene, chloroform, or a mixture thereof. PEO can form aggregates in toluene, so the solutions were warmed to ~35° C. before using. This was found by dynamic light scattering to break up any aggregates in solution.

Unless otherwise noted, these experiments were conducted with an asymmetric polystyrene-block-poly(ethylene oxide) diblock copolymer (PS-PEO; $M_n$=19 kg/mol–6.4 kg/mol). A symmetric PS-PEO block copolymer ($M_n$ of 9.5 k to 9.5 k) and a polybutadiene-block-PEO polymer ($M_n$ of 5.5 k to 5.0 k) were also used to test the generality of the observed behavior. The outer phase was 50 vol % glycerol, 50 vol % water, and 5 mg/mL polyvinyl alcohol (PVA; $M_n$~13 k to 23 k, 87%-89% hydrolyzed). The diblock copolymers stabilized the inner droplets against coalescence with the exterior aqueous phase, while PVA prevented coalescence of the oil droplets. The diblock copolymers were obtained from Polymer Source, while all other chemicals were obtained from Aldrich.

Double emulsion droplets were collected into deionized water to yield an exterior phase that was ~5% glycerol. The outer radii, $R_o$, of the double emulsions varied from about 25 micrometers to about 100 micrometers, while the internal droplet radii, $R_o$ varied from about 15 micrometers to about 50 micrometers. These values could be tuned by the size of the capillaries used. Evaporation of the solvent from double emulsions placed onto a glass slide was observed via optical microscopy. Characteristic interfacial tensions were measured by forming a pendant droplet of water at the tip of a blunt stainless steel needle immersed in a polymer solution, and fitting the Laplace equation to the measured droplet shape.

When the concentration of diblock copolymer in the middle phase was too low, stable polymerosomes could not be formed; instead, solvent evaporation lead to rupture of the organic layer and coalescence of the inner aqueous phase with the outer phase.

For typical droplet sizes ($R_i$=50 micrometers, $R_o$=70 micrometers), at 0.01 wt % polymer, complete adsorption of PS-PEO at the oil-water interfaces corresponded to an area of about 30 nm$^2$ per polymer chain. While this surface density was sufficient to stabilize the double emulsion initially, it appeared to be too sparse to form stable polymerosomes.

Figure 14A:
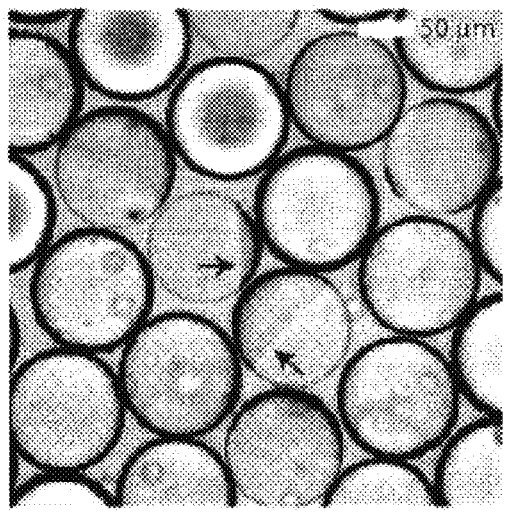
FIGS. 14A-14E illustrate certain dewetting experiments, in accordance with yet another embodiment of the invention.
Figure 14B:
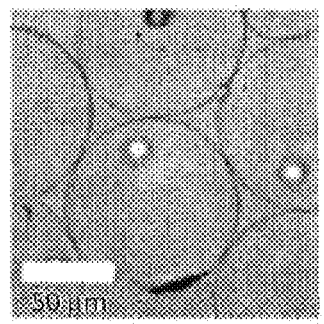

For the same droplet sizes, a polymer concentration of 0.1 wt % corresponded to an area per chain of about 3 nm$^2$, which is roughly the expected surface density in a bilayer of diblock copolymers of this molecular weight. It was observed that under these conditions, stable polymerosomes could be formed. However, a clear non-uniformity in shape was observed during solvent evaporation; the majority of the organic phase dewetted from the inner aqueous droplet, leaving behind only a thin organic film separating the inner and outer aqueous phases. Though the contact angle is low, there was a distinct contact line between the organic droplet and the thin organic film, as seen in FIG. 14A. When one of the thin organic films ruptures, it retracted as a liquid, which may imply that it remained solvated. After full solvent evaporation, a polymerosome with nearly uniform thickness and a small thicker patch of excess polymer was generated, as shown in FIG. 14B. Breakage of the polymerosome now occurs by fracture, which may be due to the glassy nature of the unsolvated PS block.

Figure 14C:
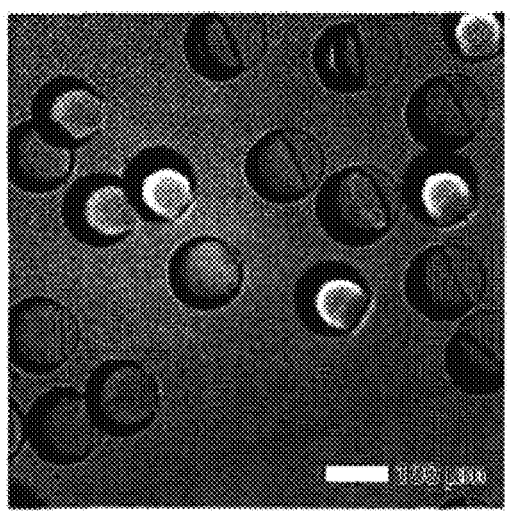
Figure 14D:
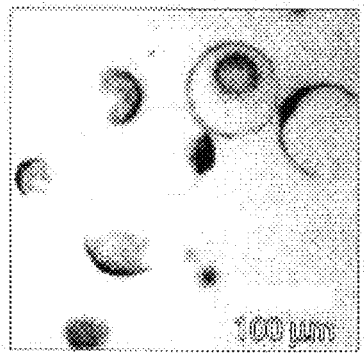

For larger polymer concentrations of 1.0 wt % to 1.5 wt %, corresponding to a large excess of diblock copolymer in the organic phase, solvent evaporation lead to dewetting with larger contact angles (FIG. 14C). Ultimately, polymerosomes with thicker patches of excess polymer were formed (FIG. 14D). The dewetting phenomenon was apparently quite general, as a symmetric PS-PEO polymer ($M_n$ of 9.5 k-9.5 k) and a polybutadiene-PEO diblock copolymer ($M_n$ of 5.5 k-5.0 k) showed nearly identical behavior; the same mechanism may thus be responsible for the inhomogeneous thicknesses in the PBA-PAA polymersomes.

Figure 14E:
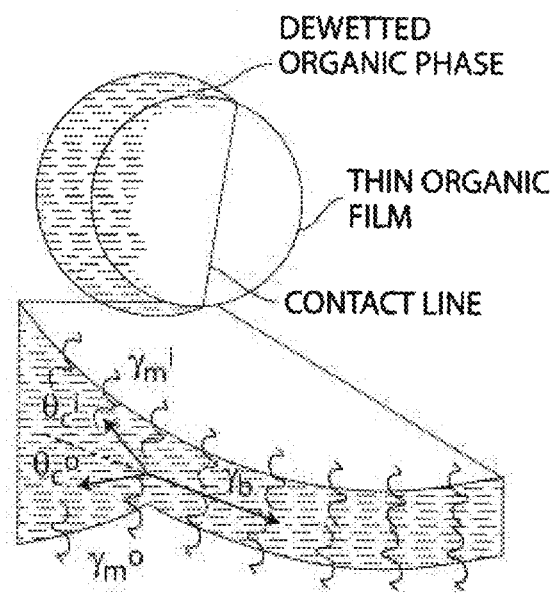

FIG. 14A is an optical micrograph revealing dewetting during solvent evaporation from a double emulsion droplet that initially was formed of an aqueous droplet surrounded by a shell of 0.1 wt % PS-PEO diblock copolymer dissolved in a toluene/chloroform mixture (2:1 by volume). Arrows indicate droplets where drainage of the organic phase to the side revealed a clear wetting line. Following complete solvent evaporation, FIG. 14B shows that the result is a thin polymerosome with a patch of excess polymer. At higher initial polymer concentrations (1.5 wt %), FIG. 14C shows that larger contact angles are evident. FIG. 14D shows homogeneous polymerosome structures formed with 1.0 wt % initial polymer content. FIG. 14E is a schematic of the structure of a double emulsion droplet with partial wetting of the organic phase on a thin layer of solvated block copolymer brushes.

The organic solvent used as the middle phase may also be important: dewetting took place when the organic solvent was purely toluene, whereas with pure chloroform, rupture and coalescence of the inner and outer aqueous phases was almost always seen. The PS-PEO diblock copolymer was not as effective as a surfactant at the water-chloroform interface as at the water-toluene interface, presumably due to the high solubility of PEO in chloroform.

These results showed that the oil phase partially dewets from the copolymer-water interface during solvent evaporation. This may be manifested as a coexistence between a thin organic layer, presumably an oil-solvated bilayer of the diblock copolymer, that is similar to a "Newton black" film encountered in soap bubbles, and a droplet of the organic phase, as shown in FIG. 14E. This implies that there is an energy of adhesion, $W_{adh}$, between the inner and outer aqueous phases, or associated polymer layers, $$\gamma_b = \gamma_m^i + \gamma_m^o - W_{adh}$$

where $\gamma_b$ represents the interfacial energy of the solvated bilayer film and $\gamma_m^i$ and $\gamma_m^o$ are the interfacial energies of the inner and outer oil-water interfaces with adsorbed polymer monolayers, respectively. Assuming that $\gamma_m^i = \gamma_m^o$, the Young-Dupré equation determining the contact angle, $\theta_c^o$, becomes:

$$W_{adh} = 2\gamma_m^o(1 - \cos\theta_c^o).$$

(In reality, the value of $\gamma_m^o$ is expected to be somewhat lower than that of $\gamma_m^i$ due to the presence of PVA at the external interface and the compression of the outer interface during solvent evaporation. As a result, the numerical factor in should be somewhere between 1 and 2.) In FIG. 14C, values of $\theta_c^o$ are as large as 35°, corresponding to $W_{adh}=0.36\gamma_m^o$. Thus, the adhesive interaction must be of the same order of magnitude as $\gamma_m^o$.

The driving force for dewetting may be a depletion interaction between the inner and outer oil-water interfaces, due to the presence of excess block copolymer in the organic phase. The magnitude of the depletion effect increases with the concentration of dissolved polymer; thus, it should become more important as solvent evaporation proceeds, and should be more apparent for higher initial polymer concentrations, as was observed. For planar hard walls, the adhesion due to depletion of a polymer solution is $$W_{adh} = a\xi\pi_{osm},$$

where $\pi_{osm}$ is the osmotic pressure, $\xi$ is the size scale of the polymer, and a is a numerical coefficient that depends on the concentration regime. In dilute polymer solutions, $\xi$ is the chain radius of gyration, $R_g$, $a=4/\sqrt{\pi}$, and $$\pi_{osm} = ck_bT,$$

where c is the number density of polymer chains. In the semi-dilute regime, $a \approx 5$, and $\xi$ corresponds to the mesh size, which scales as $c^{-3/4}$, while $\pi_{osm}$ scales as $c^{9/4}$ in a good solvent. As a result, in the dilute regime, $W_{adh} \sim c$, while in the semi-dilute regime, $W_{adh} \sim c^{3/2}$.

To estimate the magnitude of depletion interactions, the excess PS-PEO diblock copolymer is treated as a polystyrene homopolymer of the same molecular weight. Toluene and chloroform were generally good solvents for both the PS and PEO blocks, thus the PEO block was not expected to be collapsed in solution. At an excess concentration of 1.0 wt %, the previous equation gives $\pi_{osm}$=850 Pa. Using $R_g \approx 4.9$ nm, $W_{adh}$=0.0094 mN/m. This is a relatively small interaction energy; however, as solvent evaporates from the double emulsion droplets, the concentration of free PS-PEO increases, and the depletion effect becomes stronger. For example, at a concentration of 17 wt % (in the semi-dilute regime), values of $\xi$=3.2 nm, and $\pi_{osm}$=65 kPa can be calculated from data for polystyrene in toluene, yielding $W_{adh}$=1.0 mN/m.

This discussion of depletion interactions applies to hard substrates and individually solvated polymer chains. In this system, however, there were two important differences: the surfaces were not "hard," but were covered by an adsorbed "brush-like" polymer layer, and the copolymer chains may aggregate, thereby increasing $\xi$, but decreasing the number density of aggregates more rapidly, leading to a decrease in $W_{adh}$.

Polymer solutions spreading on an end-grafted "brush" of the same polymer may exhibit partial wetting (finite contact angle) or complete wetting, depending on the polymer concentration and brush grafting density. The driving force for dewetting in these systems is depletion effects, similar to those considered here. Moreover, the depletion interaction may actually be enhanced on brushlike polymeric substrates, since the thickness of the exclusion zone is larger, the sum of the free chain dimension and the brush layer. By contrast, any aggregation of the PS-PEO diblock copolymer would reduce $W_{adh}$. To check for aggregates, dynamic light scattering (DLS) was used. It was found that a dilute solution of 5 mg/mL of PS-PEO in toluene was formed primarily of unimers with hydrodynamic radii $R_h$~4 nm. This value compared favorably with the estimate of $R_g$=4.9 nm used in calculating the magnitude of depletion effects, given the inaccuracy of DLS for determining such small sizes.

However, after coming into contact with water, a population of aggregates centered around $R_h$~35 nm (presumably microemulsion droplets) appeared, as well as a distribution of larger aggregates with $R_h$>100 nm. In addition, optical microscopy revealed large aggregates of about 1 micrometer to 5 micrometers in the oil phase; these are apparently spontaneously-formed water-in-oil emulsion droplets. This aggregation may lessen the strength of the depletion interaction.

An important feature of this behavior is that the adhesive interaction may be comparable to the interfacial tension of the block-copolymer-covered oil-water interface. Therefore, these estimates of the depletion interaction were compared to independent measurements of the interfacial tension, $\gamma$, between water and solutions of PS-PEO in toluene. At 0.1 wt % and 1 wt % polymer, the value of $\gamma$ leveled off to 1 mN/m to 2 mN/m within 30 min. At 0.01 wt %, a similar value was attained within 4 h. The limiting value varied somewhat between measurements (±0.5 mN/m) but did not depend strongly on block copolymer concentration in the range of 0.01 wt % to 1 wt %. Thus, the value of the measured surface tension was indeed of the same magnitude as the estimates of the depletion interaction in the semidilute regime, provided large aggregates did not form.

Figure 15A:
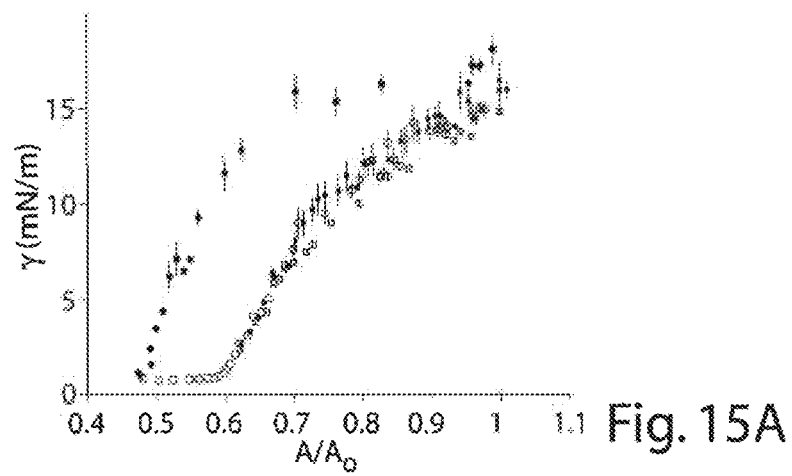
FIGS. 15A-15B are graphs illustrating interfacial tension experiments in another embodiment of the invention.

During solvent evaporation from the double emulsion droplets, the shrinking area of the external oil-water interface may lead to non-equilibrium effects that further lower the interfacial tension. To understand how the block copolymer responds as the interfacial area shrinks, polymer was allowed to adsorb to a pendant water droplet for 5 minutes, followed by removal of water at a constant volumetric rate. As the surface area of the droplet decreased, the interfacial tension was observed decreased as well. If the compression was stopped with $\gamma$ above 1 mN/m, expansion re-traces the path of compression with little hysteresis. However, when the droplet surface was compressed further, a plateau in $\gamma$ is reached at ~1 mN/m, as seen in FIG. 15A. The plateau may reflect desorption of polymer from the interface when driven below the equilibrium area per chain. Compression into the plateau region gave rise to hysteresis, as seen in FIG. 15A, indicating that polymer may be removed from the interface during compression. More specifically, FIG. 14A illustrates the interfacial tension ($\gamma$) between water and toluene containing 0.1 wt % PS-PEO as a function of normalized droplet surface area (A/A0) for two different compression-expansion isotherms. Open symbols correspond to compression, closed to expansion. For the squares, compression was stopped prior to reaching the plateau in surface tension, while for the circles, compression was continued past the onset of the plateau.

Figure 15B:
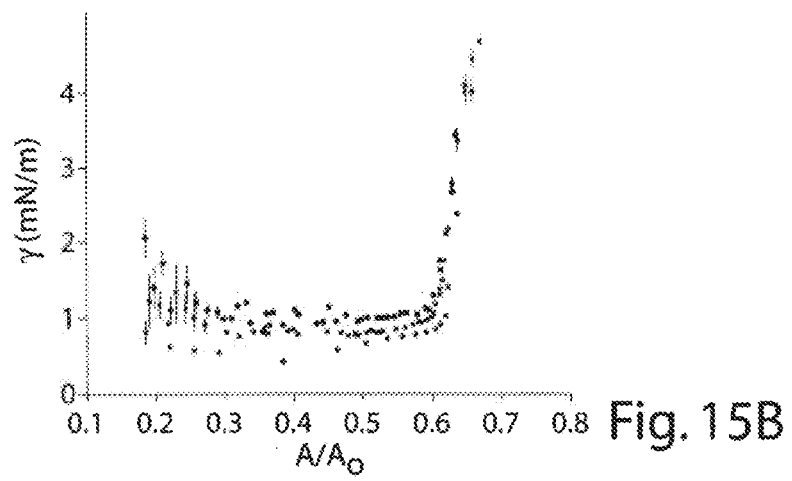

The rate of compression (or evaporation) may also be important: faster compression lead to a lower plateau value, as shown in FIG. 15B. Solvent evaporation from the double emulsion droplets typically corresponds to characteristic deformation rates of $10^{-4}$ Hz to $10^{-2}$ Hz. Thus, the interfacial tension of the shrinking oil-water interface in the case of the double emulsion system may be driven somewhat below its equilibrium value, but can be expected to remain in the range of 0.5 mN/m to 1 mN/m at low concentrations of PS-PEO. The presence of PVA at the outer oil-water interface may also be important during solvent evaporation from double emulsion droplets. However, compression isotherms with both PVA and PS-PEO present suggests that PS-PEO dominates the surface behavior. More specifically, FIG. 15B illustrates Compression isotherms at different rates of water withdrawal from a 5 microliter droplet: 0.1 microliter/min (circles), 1 microliter/min (squares), 10 microliter/min (diamonds). A rough characterization of the surface deformation rate is given by the average rate of change of area over the compression, normalized by the area in the middle of the plateau region. These values correspond to ~0.002 Hz (circles), ~0.02 Hz (squares), and ~0.2 Hz (diamonds). Error bars represent 95% confidence intervals of the values of surface tension, as fitted by non-linear least squares analysis.

In some cases, the organic phase can essentially completely dewets the inner water droplet during solvent evaporation. Continued solvent evaporation from the organic droplets lead to an interfacial instability, as shown in FIG. 15, wherein the large droplet spontaneously broke up into many smaller droplets. Apparently, at sufficiently high polymer concentrations and rates of solvent evaporation, the value of $\gamma$ can become arbitrarily small, and can even become negative. In such cases of vanishing interfacial tension, the presence of even a very small adhesive interaction may be sufficient to drive dewetting. For example, Van der Waals interactions may give rise to an adhesion energy per unit area of $W_{adh}$=A/(12$\pi$h$^2$), where A is the Hamaker constant, (about 10-20 J for water-hydrocarbon-water systems), and h is the thickness of the oil film. Using 15 nm as an estimate for h gives $W_{adh}$=0.001 mN/m. This is smaller than the characteristic value of $\gamma$ of order 1 mN/m, as well as the estimated magnitude of the depletion interaction. However, the observation of vanishing interfacial tension suggests that even Van der Waals forces may be large enough to drive dewetting under some conditions.

Figure 16:
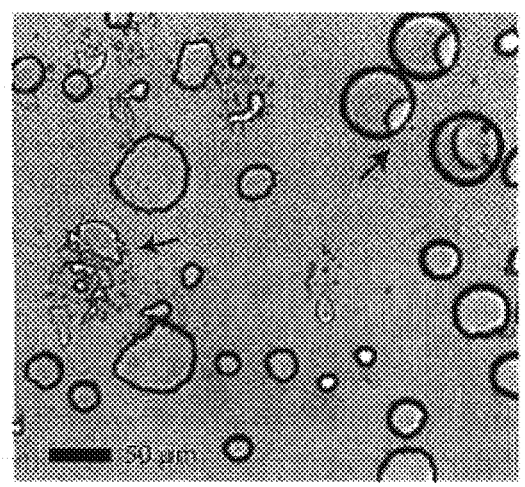
FIG. 16 is a copy of a photomicrograph showing certain dewetted droplets of the invention.

FIG. 16 shows that under some conditions, solvent evaporation lead to dewetting of the organic phase with contact angles approaching 180° (upper right). Further solvent evaporation from organic droplets that have completely detached from the inner aqueous droplets lead to an interfacial instability causing breakup into smaller droplets (left side).

In conclusion, when forming polymerosomes from double emulsion templates, it may be important to consider wetting of the organic phase on the polymer brushes at the oil-water interface. In order to avoid a dewetting instability in the presence of excess polymer, it may be necessary to carefully control the interfacial tension by adjusting the strength of adsorption of the polymer at the oil-water interfaces and the rate of solvent evaporation. In addition, it may be important to independently control the osmotic pressure of the organic phase as solvent evaporation increases the concentration of nonvolatile components, for example, through their size or state of aggregation.

This invention is not limited in its application to the details of construction and the arrangement of components set forth in the following description or illustrated in the drawings. The invention is capable of other embodiments and of being practiced or of being carried out in various ways. Also, the phraseology and terminology used herein is for the purpose of description and should not be regarded as limiting. Thus, while several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present invention.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one." The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed is:

1. A method of making a droplet comprising:
   forming a multiple emulsion droplet from a first fluid stream flowing in a first direction contained within a first microfluidic channel and a second fluid stream flowing substantially in the first direction contained within a second microfluidic channel, by simultaneously surrounding a portion of the first fluid stream with a portion of the second fluid stream, the portion of the first fluid stream in contact with the portion of the second fluid stream, while surrounding the portion of the second fluid stream with a third fluid upon contact with a third fluid stream flowing within the second microfluidic channel in a second direction that is substantially opposed to the first direction, and altering the direction of flow of the third fluid stream to flow substantially in the first direction upon contact of the third fluid stream with the second fluid stream, wherein the multiple emulsion droplet comprises a droplet of the first fluid, contained within a droplet of the second fluid, surrounded by the third fluid.

2. The method of claim 1, wherein the first fluid is miscible in the third fluid.

3. The method of claim 1, wherein the second fluid comprises a material selected from surfactants, prepolymers, polymers, lipids, copolymers and amphiphiles.

4. The method of claim 3, wherein the copolymer is a diblock copolymer, a triblock copolymer and/or a random copolymer.

5. The method of claim 1, wherein the first and second fluids form a polymerosome or a liposome.

6. The method of claim 1, further comprising causing formation of a hardened shell in the droplet of the second fluid within the multiple emulsion droplet after formation of the multiple emulsion droplet.

7. The method of claim 1, wherein the multiple emulsion droplet comprises a plurality of droplets of the first fluid inside the droplet of the second fluid.

8. A method comprising:
flowing a first fluid stream exiting a first microfluidic channel in a first direction;
flowing a second fluid stream contained within a second microfluidic channel in a direction substantially in the first direction, the second stream circumscribing the first stream upon exiting of the first fluid stream from the first microfluidic channel, the first microfluidic channel being disposed in the second microfluidic channel;
flowing a third fluid stream within the second microfluidic channel in a second direction that is substantially opposed to the first direction; and
altering the direction of flow of the third fluid stream to flow substantially in the first direction upon contact with the second fluid.

9. The method of claim 8, wherein at least a portion of the third stream circumscribes a portion of the second stream.

10. The method of claim 8, wherein the fluid of the first stream is miscible in the fluid of the third stream.

11. A method of packaging a species comprising:
suspending a species in a first fluid;
flowing the first fluid in a stream in a first direction;
surrounding a portion of the first fluid with a portion of a second fluid upon contact of the first fluid stream with a second fluid stream flowing substantially in the first direction, the second fluid being substantially immiscible with the first fluid;
introducing a third fluid stream flowing in a direction substantially opposed to the first direction; and
altering the direction of flow of the third fluid stream to flow substantially in the first direction upon contact of the third fluid stream with the second fluid stream, the third fluid stream surrounding the second fluid stream upon contact; and
forming multiple droplets of the first fluid wherein the droplets contain at least one of the species.

12. The method of claim 11, wherein the species is selected from cells, drugs, nucleic acids, proteins, fragrances, nanoparticles and quantum dots.

13. The method of claim 11, further comprising solidifying a portion of the second fluid surrounding the droplet.

14. The method of claim 11, comprising solidifying at least a portion of the inner droplet.

15. A method for forming droplets, comprising:
flowing a first fluid in a first direction in a first microfluidic conduit having a first diameter;
flowing a second fluid in substantially the first direction in a second microfluidic conduit having an end defining an exit opening, wherein the second microfluidic conduit is disposed in the first microfluidic conduit;
expelling the second fluid, from the exit opening of the second conduit, into the first fluid in the first microfluidic conduit;
surrounding the first and second fluids with a third fluid upon contact with a third fluid stream flowing in a second direction that is substantially opposed to the first direction;
altering the direction of flow of the third fluid stream to flow substantially in the first direction upon contact with the first fluid;
advancing the second fluid, surrounded by the first fluid, into a restriction under conditions in which droplets of the second fluid in the first fluid are formed within the restriction; and
releasing the droplets of the second fluid carried in the first fluid from the restriction into a region of dimension larger than the restriction.

16. The method of claim 15, wherein the second fluid surrounds a fourth fluid.

* * * * *